United States Patent
Chang et al.

(10) Patent No.: US 11,959,875 B2
(45) Date of Patent: Apr. 16, 2024

(54) COMPOSITION, ELECTRODE, AND FABRICATION METHOD FOR PHOSPHATE SENSING

(71) Applicant: UWM Research Foundation, Inc., Milwaukee, WI (US)

(72) Inventors: Woo-Jin Chang, Whitefish Bay, WI (US); Misong Ryu, Milwaukee, WI (US); Mohammad Rizwen Ur Rahman, Milwaukee, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 344 days.

(21) Appl. No.: 16/631,104

(22) PCT Filed: Aug. 10, 2018

(86) PCT No.: PCT/US2018/046322
§ 371 (c)(1),
(2) Date: Jan. 14, 2020

(87) PCT Pub. No.: WO2019/033034
PCT Pub. Date: Feb. 14, 2019

(65) Prior Publication Data
US 2020/0158682 A1    May 21, 2020

Related U.S. Application Data

(60) Provisional application No. 62/544,343, filed on Aug. 11, 2017.

(51) Int. Cl.
*G01N 27/333* (2006.01)
*G01N 27/30* (2006.01)
(Continued)

(52) U.S. Cl.
CPC ......... *G01N 27/333* (2013.01); *G01N 27/307* (2013.01); *G01N 27/308* (2013.01); *G01N 27/48* (2013.01); *G01N 33/182* (2013.01)

(58) Field of Classification Search
CPC .. G01N 27/307; G01N 27/308; G01N 33/182; G01N 27/333; G01N 27/48
See application file for complete search history.

(56) References Cited

U.S. PATENT DOCUMENTS

| | | | |
|---|---|---|---|
| 4,900,404 A | 2/1990 | Arnold et al. | |
| 2007/0092972 A1* | 4/2007 | Xiao | G01N 21/78 |
| | | | 436/103 |
| 2017/0363572 A1 | 12/2017 | Gunasekaran et al. | |

FOREIGN PATENT DOCUMENTS

| | | |
|---|---|---|
| CN | 103940881 A | 7/2014 |
| CN | 104267080 A | 1/2015 |
| (Continued) | | |

OTHER PUBLICATIONS

Nia et al., Electrodeposition of copper oxide/polypyrrole/reduced graphene oxide as a nonenzymatic glucose biosensor, Sensor and Actuators B: Chemical, vol. 209, pp. 100-108 (2015) (Year: 2015).*

(Continued)

*Primary Examiner* — Joshua L Allen
*Assistant Examiner* — Vivian A Tran
(74) *Attorney, Agent, or Firm* — Michael Best & Friedrich LLP

(57) ABSTRACT

Composition and electrode for phosphate sensing. In one embodiment, the composition includes a first component, a second component, and a third component. The first component is selected from a group consisting of cobalt oxide nanoparticles, tin (IV) chloride, diphenyl tin dichloride, and ammonium molybdate. The second component includes (Continued)

graphene oxide or reduced graphene oxide. The third component includes pyrrole or polypyrrole.

8 Claims, 34 Drawing Sheets

(51) Int. Cl.
  *G01N 27/48* (2006.01)
  *G01N 33/18* (2006.01)

(56) References Cited

FOREIGN PATENT DOCUMENTS

| CN | 104851611 A | * | 8/2015 |
|---|---|---|---|
| CN | 104851611 A | | 8/2015 |
| GB | 2503689 A | | 1/2014 |
| WO | WO2012074368 A1 | | 6/2012 |
| WO | WO2012154028 A1 | | 11/2012 |
| WO | WO2016032314 A1 | | 3/2016 |

OTHER PUBLICATIONS

Ryu et al., Low-cost disposable sensor for detection of phosphate using cobalt oxide nanoparticles drop casting, Conference: IEEE Milwaukee Section 2016 Larry Hause Student Poster Competition, Milwaukee School of Engineering Todd Wehr Conference Center (2016) (Year: 2016).*
Ambrosi et al., Electrochemistry at Chemically Modified Graphenes, Chemistry A European Journal, vol. 17, Issue 38, pp. 10763-10770 (2011) (Year: 2011).*
Berchmans, Determination of inorganic phosphate by electroanalytical methods: A review, Analytical Chimica Acta, vol. 729, pp. 7-20 (2012) (Year: 2012).*
Yang et al., Supercritical CO2-assisted preparation of 3D graphene-pyrrole/carbon nanotubes/polyaniline Nanoarchitectures for efficient supercapacitor electrodes, Materials Letters, vol. 139, pp. 471-474 (2015) (Year: 2015).*
Fisher Scientific "Stannous Chloride Reagent II, for Phosphate Analysis (with Extraction)." [Online]. Available: https://www.fishersci.com/shop/products/stannous-chloride-reagent-ii-phosphate-analysis-with-extraction-ricca-chemical-3/799816. [Accessed: Dec. 31, 2017].
Antonisse et al., "Potentiometric Anion Selective Sensors," Electroanalysis, vol. 11, No. 14, pp. 1035-1048, Oct. 1999.
Berchmans et al., "Determination of inorganic phosphate by electroanalytical methods: A review," Anal. Chim. Acta, vol. 729, pp. 7-20, 2012.
Chang et al., "Electrochemical Phosphate Sensor," Poster, OTT#1513, UWM Research Foundation, Apr. 8, 2018, pp. 1-11, Retrieved from Internet: https://uwmrf.org/wp-content/uploads/2018/04/OTT1513-Phosphate-Sensor-Slides-2018.pdf.
Chang et al., "Graphene-based sensors for detection of heavy metals in water: a review," Anal. Bioanal. Chem., vol. 406, No. 16, pp. 3957-3975, 2014.
Chang, Low-cost electrochemical water sensors, Milwaukee Engineering Research Conference, May 5-6, 2016, UW-Milwaukee, WI.
Cilley, "Solubility of tin(II) orthophosphate and the phosphate complexes of tin(II)," Inorg. Chem., vol. 7, No. 3, pp. 612-614, Mar. 1968.
Cinti et al., "Novel carbon black-cobalt phthalocyanine nanocomposite as sensing platform to detect organophosphorus pollutants at screen-printed electrode," Electrochim. Acta, vol. 188, pp. 574-581, 2016.
Cinti et al., "Novel Reagentless Paper-based Screen-printed Electrochemical Sensor to Detect Phosphate," Analytica Chimica Acta, vol. 919, pp. 78-84 (2016).
De Marco et al., "Determination of phosphate in hydroponic nutrient solutions using flow injection potentiometry and a cobalt-wire phosphate ion-selective electrode.," Talanta, vol. 60, No. 6, pp. 1215-1221, Aug. 2003.
Demeulenaere et al., "Selectivity for Phosphate and Citrate with Benzyltin-Based Polymer Membrane Electrodes," Electroanalysis 5, 1993, 833-838.
Devadas et al., "Electrochemically Reduced Graphene Oxide/ Neodymium Hexacyanoferrate Modified Electrodes for the Electrochemical Detection of Paracetomol," Int. J. Electrochem. Sci, vol. 7, pp. 3339-3349, 2012.
Fanjulbolado et al., "Manufacture and evaluation of carbon nanotube modified screen-printed electrodes as electrochemical tools," Talanta, vol. 74, No. 3, pp. 427-433, Dec. 2007.
Gan et al., "Electrochemical sensors based on graphene materials," Microchim. Acta, vol. 175, No. 1-2, pp. 1-19, Oct. 2011.
Gilmore "Laboratory Studies in Chemically Mediated Phosphorus Removal," Theses Diss., Jan. 2009.
Glazier et al., "Selectivity of membrane electrodes based on derivatives of dibenzyltin dichloride.," Anal. Chem., vol. 63, No. 8, pp. 754-759, 1991.
Hanna Instruments, "Phosphate Low Range Portable Photometer," <https://www.hannainst.com/hi96713-phosphate-low-range-portable-photometer.html> web page available at least as early as Feb. 8, 2016.
Henriksen, "Application of a modified stannous chloride reagent for determining orthophosphate," Analyst, vol. 88, No. 1052, p. 898, Jan. 1963.
Horwitt, "Determination of inorganic serum phosphate by means of stannous chloride," J. Biol. Chem., vol. 199, No. 2, pp. 537-541, Jun. 1952.
International Preliminary Report on Patentability for Application No. PCT/US2018/046322 dated Feb. 20, 2020 (13 pages).
International Search Report and Written Opinion for Application No. PCT/US2018/046322 dated Nov. 27, 2018 (15 pages).
Javier et al. "Investigations of formation of 12-molybdophosphoric acid utilizing rapid reaction-rate measurements," Anal. Chem., vol. 40, No. 13, pp. 1922-1925, Nov. 1968.
Law Al et al., "Progress and recent advances in phosphate sensors: A review," Talanta, vol. 114, pp. 191-203, 2013.
Lee et al., "Characteristics of a cobalt-based phosphate microelectrode for in situ monitoring of phosphate and its biological application," Sensors Actuators B Chem., vol. 137, No. 1, pp. 121-128, Mar. 2009.
Li et al., "Phosphate Sensor using molybdenum," Journal of Electrochemical Society, vol. 163, pp. B479-B484 (2016).
Li et al., "Recent advances on synthesis and application of graphene as novel sensing materials in analytical chemistry," Rev. Anal. Chem., vol. 31, No. 1, pp. 57-81, Jan. 2012.
Li et al., "Recent developments and applications of screen-printed electrodes in environmental assays—A review," Anal. Chim. Acta, vol. 734, pp. 31-44, 2012.
Meruva et al., "Mixed Potential Response Mechanism of Cobalt Electrodes toward Inorganic Phosphate," Anal. Chem., vol. 68, No. 13. pp. 2022-2026, 1996.
Nia et al. "Electrodepsition of copper oxide/polypyrrole/reduced graphene oxide as a nonenzymatic glucose biosensor," Sensors and actuators B: Chemical, vol. 209, pp. 100-108 (2015).
Rahman et al., Fabrication and characterization of low-cost disposable electrochemical sensor for detecting heavy metals using polypyrrole and Cysteinefunctionalized Graphene oxide, UWM CEAS Poster Competition, Apr. 23, 2016, UW-Milwaukee, WI.
Ryu et al., Interference of KCl on Cobalt Nanoparticle-based Electrochemical Low-cost Disposable Phosphate Sensor, BMES 2016 Annual Meeting, Poster, Oct. 5-8, 2016, Minneapolis, MN.
Ryu et al., Low-cost disposable sensor for detection of phosphate using cobalt nanoparticles drop casting, IEEE Milwaukee Section 2016 Larry Hause Student Poster Competition, May 12, 2016, Milwaukee, WI.
Seenivasan et al., Highly Sensitive Detection and Removal of Lead Ions in Water using Cysteine-Functionalized Graphene Oxide/ Polypyrrole Nanocomposite Film Electrode, ACS Applied Materials & Interfaces, 7(29), 15935-15943, 2015.
Sletten et al., "Modified Stannous Chloride Reagent for Orthophosphate Determination," Journal (American Water Works Association), vol. 53. American Water Works Association, pp. 1031-1033, 1961.

(56) References Cited

OTHER PUBLICATIONS

Song et al., "A disposable cobalt-based phosphate sensor based on screen printing technology," Sci. China Chem., vol. 57, No. 9, pp. 1283-1290, 2014.

Talarico et al., "Phosphate Detection through a Cost-Effective Carbon Black Nanoparticle-Modified Screen-Printed Electrode Embedded in a Continuous Flow System," Environ. Sci. Technol., vol. 49, No. 13, pp. 7934-7939, 2015.

Talarico et al., "Screen-printed electrode modified with carbon black nanoparticles for phosphate detection by measuring the electroactive phosphomolybdate complex," Talanta, vol. 141, pp. 267-272, 2015.

Thiyagarajan et al., "Disposable electrochemical sensors: A mini review," Electrochem. commun., vol. 38, pp. 86-90, 2014.

Wang et al., "High Mobility, Printable, and Solution-Processed Graphene Electronics," Nano Lett., vol. 10, No. 1, pp. 92-98, Jan. 2010.

Xiao et al., "Surface-modified Cobalt-Based Sensor as a Phosphate-Sensitive Electrode," Analytical Chemistry, vol. 67, pp. 288-291 (1995).

Yang et al., "Digital pH Test Strips for In-Field pH Monitoring Using Iridium Oxide-Reduced Graphene Oxide Hybrid Thin Films," ACS Sensors, vol. 1, No. 10, pp. 1235-1243, Oct. 2016.

Yang et al., "Iridium Oxide-reduced Graphene Oxide Nanohybrid Thin Film Modified Screen-printed Electrodes as Disposable Electrochemical Paper Microfluidic pH Sensors," J. Vis. Exp., No. 117, pp. e53339-e53339, Nov. 2016.

Zhu et al., "A potentiometric Cobalt-based Phosphate Sensor Based on Screen-printing Technology," Front. Environ. Sci. Eng., vol. 8, pp. 945-951 (2014).

\* cited by examiner

COMPOSITION, ELECTRODE, AND FABRICATION METHOD FOR PHOSPHATE SENSING

CROSS-REFERENCE TO RELATED APPLICATIONS

This patent application is the U.S. national stage entry, under 35 U.S.C. § 371, of International Application Number PCT/US2018/046322, filed Aug. 10, 2018, which claims priority to U.S. Provisional Application No. 62/544,343, entitled "DETECTION OF PHOSPHATE IN WATER," filed Aug. 11, 2017, the entire contents of each of which are hereby incorporated by reference.

STATEMENT REGARDING FEDERALLY SPONSORED RESEARCH OR DEVELOPMENT

This invention was made with government support under grant No. IIP-0968887 awarded by the National Science Foundation. The Government has certain rights in the invention.

BACKGROUND

Phosphate ($PO_4^{-3}$) is a chemical compound containing phosphorus, and a non-metallic essential plant nutrient necessary for growth of plants and animals. Calcium hydrogen phosphate ($CaH_4P_2O_8$) is a major component of many fertilizers widely known as "Superphosphate." Phosphorus is the eleventh most abundant mineral in the earth's crust and plays important roles in deoxyribonucleic acid (DNA), ribonucleic acid (RNA), adenosine diphosphate (ADP), and adenosine triphosphate (ATP). However, too much nitrogen and phosphorus enter the environment—usually from a wide range of human activities—pollute the air and water. Too much nitrogen and soluble reactive phosphate (i.e. phosphorus) in the water are often responsible for eutrophication (excessive aquatic plant growth) of lakes, reservoirs, and streams. Substantial growth of algae deteriorates water quality, damages food resources, and habitats of fish and other aquatic life. Most importantly, eutrophication severely reduces or eliminates oxygen in the water, leading to illnesses in fish and the death of large numbers of fish. Nutrient pollution has impacted many streams, rivers, lakes, bays and coastal waters for the past several decades, resulting in serious environmental and human health issues and economy. Algae blooms may contain blue-green algae (cyanobacteria) that release toxins into the water, as happened in Lake Erie, U.S.A. in the summer of 2014. This made the water from the Toledo water treatment plant unhealthy to drink for several days.

Phosphate itself is not toxic and the health effects of phosphates in drinking water with phosphates on health are not known. A report on the toxicology of inorganic phosphates as food ingredients issued by the Food and Drug Administration (FDA) stated phosphates generally recognized as safe as a food additive. NSF International maintains recommended maximum dosages of phosphate products in drinking water along with other additives for water treatment. The typical phosphate levels found in an average American diet is about hundred times higher than the phosphate levels found in a liter of drinking water (0.025 mg/L). For example, within the recommended limit of phosphates in the water, the amount of phosphates in one can of soda is equal to about twelve liters of water.

Phosphates are commonly added as a corrosion/rust inhibitor to the drinking water by the Public water systems (PWSs) to prevent the leaching of lead and copper from metal pipes and fixtures. Inorganic phosphates (for example, phosphoric acid, zinc phosphate, and sodium phosphate) form orthophosphate when added to the water, create a protective coating of insoluble mineral on the inside of pipes/service lines and household plumbing. The coating prevents dissolving of corrosion elements from metal complexes on the metal pipes. The PWSs maintain the suitable orthophosphate levels (about 300 ppb) to reduce corrosion based on the supply water quality.

Phosphate in water can form inorganic and/or organic phosphorus due to its nature and available in particulate phase or a dissolved phase. Particulate matter includes living and dead plankton, precipitates of phosphorus, phosphorus adsorbed to particulates, and amorphous phosphorus. The dissolved phase includes inorganic phosphorus (generally in the soluble orthophosphate form), organic phosphorus excreted by organisms, and macromolecular colloidal phosphorus. The organic and inorganic particulate and soluble forms of phosphorus undergo continuous transformations. The dissolved phosphorus (usually as orthophosphate) is assimilated by phytoplankton and altered to organic phosphorus. There are many sources of phosphates, both natural and human. Phosphates end up in water by runoff from farming fields, lawns and golf-courses treated with phosphate-containing fertilizers, livestock and poultry-feeding operations, pet wastes, food-processing wastes, wastewater from the pulp and paper industry, and partially treated or untreated sewage. All phosphorus eventually converted to the inorganic forms through several biological reactions in the environment. Soluble phosphorus in natural water may present in four states based on the pH: $H_3PO_4$ (phosphoric acid), $H_2PO_4^-$ (dihydrogen phosphate), $H_2PO_4^{2-}$ (hydrogen phosphate), and $PO_4^{3-}$ (orthophosphate). The EPA and the Department of Natural Resources has set specific guidelines for effluent water stream from industries to rivers, lakes, and watersheds. The soluble reactive phosphate concentration of around 0.05 mg/L may trigger an algal bloom. Dissolved phosphate is another concern in drinking water quality. Phosphate levels greater than 1.0 ppm (mg/L) may interfere with coagulation in water treatment plants. Thus, monitoring of phosphate concentration is very important for maintaining water quality and minimizing nutrient pollution. Development of an inexpensive, sensitive, small-size phosphate sensor is needed for continuous and on-site monitoring to effectively control industrial effluent and drinking water.

SUMMARY

The disclosure provides a composition for phosphate sensing. In one embodiment, the composition includes a first component, a second component, and a third component. The first component is selected from a group consisting of cobalt oxide nanoparticles, tin (IV) chloride, diphenyl tin dichloride, and ammonium molybdate. The second component includes graphene oxide or reduced graphene oxide. The third component includes pyrrole or polypyrrole.

The disclosure also provides an electrode for phosphate sensing. In one embodiment, the electrode includes a conductive layer and a first layer. The first layer is electrically connected to the conductive layer. The first layer includes a first component. The first component is selected from a group consisting of cobalt oxide nanoparticles, tin (IV) chloride, diphenyl tin dichloride, and ammonium molybdate.

The disclosure further provides a method for fabricating an electrode for phosphate sensing. The method includes the step of providing a screen-printed electrode. The screen-printed electrode includes a working electrode. The working electrode includes a conductive surface. The method also includes the step of depositing a first layer onto the conductive surface. The first layer includes a first component. The first component is selected from a group consisting of cobalt oxide nanoparticles, tin (IV) chloride, diphenyltin dichloride, and ammonium molybdate.

Other aspects of the disclosure will become apparent by consideration of the detailed description and accompanying drawings.

BRIEF DESCRIPTION OF THE DRAWINGS

FIGS. 109A-10D are scanning electron microscopy (SEM) images of the cobalt doped sensor surface (×400); 1.5 mg/mL (FIG. 10A), 3 mg/mL (FIG. 10B), 6 mg/mL (FIG. 10C), 9 mg/mL (FIG. 10D).

(FIG. 26A), and an interference study of phosphate ions in presence of Cl— ions (FIG. 26B).

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways.

The phrase "essentially free" as used herein refers a composition that includes less than one percent of the element which the composition is "essentially free" of. For example, a composition that includes a first element and is "essentially free" of a second element may include trace amounts (i.e., less than one percent) of the second element.

Figure 1:
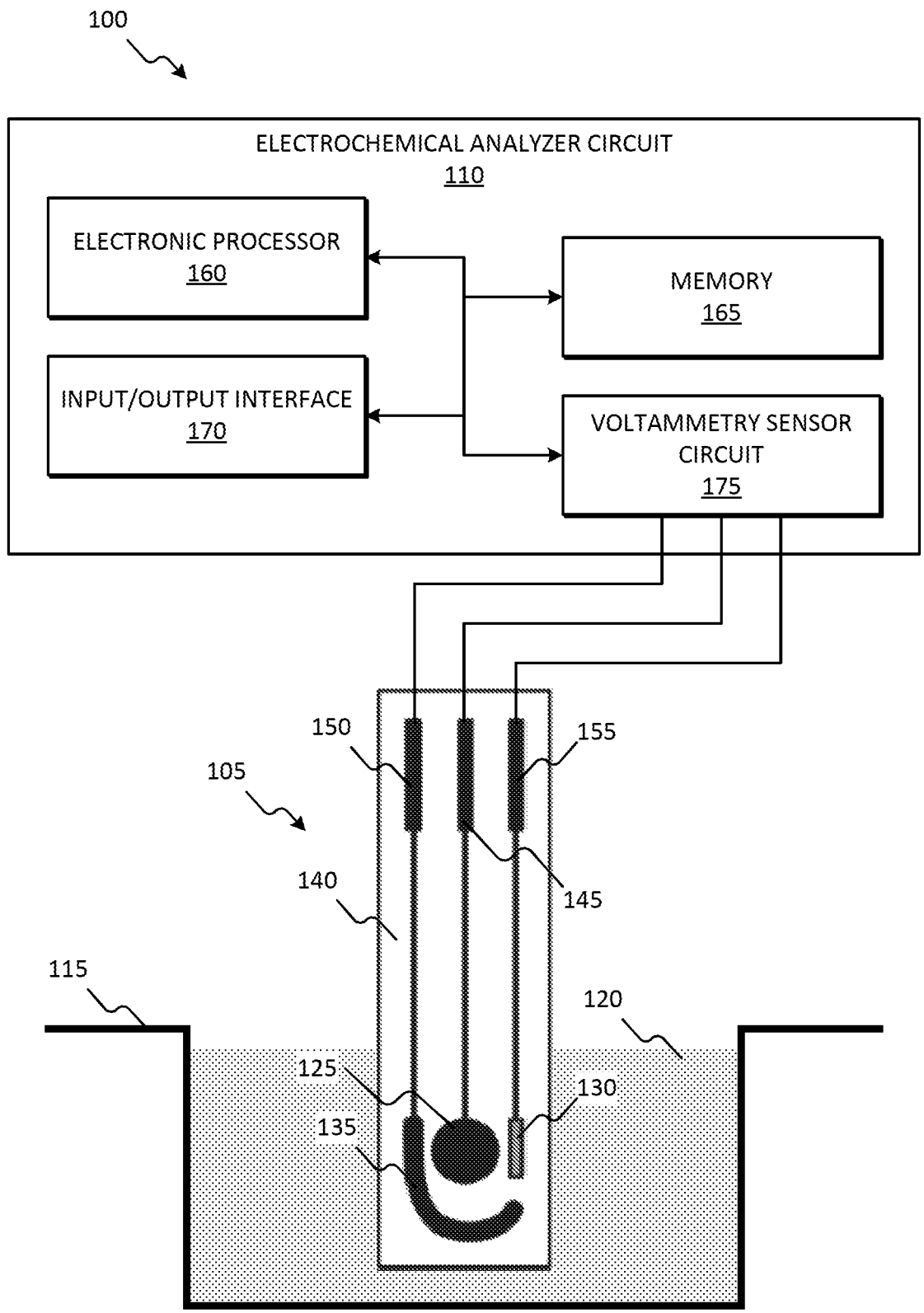
FIG. 1 is a diagram of an phosphate sensing system, in accordance with some embodiments.

FIG. 1 is a diagram of one example embodiment of a phosphate sensing system 100. In the embodiment illustrated, the phosphate sensing system 100 includes a screen-printed electrode 105 and an electrochemical analyzer circuit 110. The screen-printed electrode 105 generates a voltage potential due to the electrochemical reaction of an analyte on the screen-printed electrode 105. For example, the screen-printed electrode 105 generates a voltage potential due to the oxidation reaction caused when the screen-printed electrode 105 is submerged in a container 115 containing a solution 120 (or sample) that includes phosphate, as illustrated in FIG. 1. The potential of the screen-printed electrode 105 equilibrates with the solution 120 so that no current flows. The potential observed when no current is flowing is called the open circuit potential (OCP). In some embodiments, the solution 120 is collected from a natural environment and/or a residential source. In some embodiments, the solution 120 includes run-off water collected near a farm. In some embodiments, the solution 120 is a liquid. In some embodiments, all (or a portion) of the phosphate sensing system 100 is hand-held.

The screen-printed electrode 105 includes a working electrode 125, a reference electrode 130, a counter electrode 135, a substrate 140, and leads 145, 150, and 155. The working electrode 125 carries out the electrochemical event of interest. The reference electrode 130 has a well-defined and stable equilibrium potential and is used as a reference point against which the potential of other electrodes can be measured. In some embodiments, the reference electrode 130 includes silver (Ag) or silver chloride (AgCl). When a potential is applied to the working electrode 125 such that oxidation of the analyte can occur, current begins to flow. The purpose of the counter electrode 135 is to complete the electrical circuit. Current is recorded as electrons flow between the working electrode 125 and the counter electrode 135. In some embodiments, the counter electrode 135 includes graphitic carbon.

In the embodiment illustrated, the electrochemical analyzer circuit 110 includes an electronic processor 160 (for example, a microprocessor, or other electronic controller), memory 165, an input/output interface 170, and a voltammetry sensor circuit 175, and a bus. In alternate embodiments, the electrochemical analyzer circuit 110 may include fewer or additional components in configurations different from the configuration illustrated in FIG. 1. The bus connects various components of the electrochemical analyzer circuit 110 including the memory 165 to the electronic processor 160. The memory 165 includes read only memory (ROM), random access memory (RAM), an electrically erasable programmable read-only memory (EEPROM), other non-transitory computer-readable media, or a combination thereof. The electronic processor 160 is configured to retrieve program instructions and data from the memory 165 and execute, among other things, instructions to perform the methods described herein. Alternatively, or in addition to, the memory 165 is included in the electronic processor 160.

The input/output interface 170 includes routines for transferring information between components within the electrochemical analyzer circuit 110 and other components of the phosphate sensing system 100, as well as components external to the phosphate sensing system 100. The input/output interface 170 is configured to transmit and receive signals via wires, fiber, wirelessly, or a combination thereof. Signals may include, for example, information, data, serial data, data packets, analog signals, or a combination thereof.

The voltammetry sensor circuit 175 is coupled to the leads 145, 150, and 155 of the screen-printed electrode 105 and is configured to measure the voltage potential between the working electrode 125 and the reference electrode 130 generated, for example, by phosphate placed on the screen-printed electrode 105 (for example, the open circuit potential). The voltammetry sensor circuit 175 is configured to transmit a signal indicating a voltage potential that corresponds to a concentration of phosphate in the solution 120. The voltammetry sensor circuit 175 includes, for example, a potentiostat, filters, digital to analog converters, attenuators, current to voltage converters, amplifiers, or a combination thereof.

In some embodiments, the working electrode 125 includes graphitic carbon. In some embodiments, a composition for phosphate sensing is connected to the working electrode 125. In some embodiments, the composition includes a first component, a second component, and a third component. The first component is selected from a group consisting of cobalt oxide nanoparticles, tin (IV) chloride, diphenyl tin dichloride, and ammonium molybdate. The second component is either graphene oxide or reduced graphene oxide. The third component is either pyrrole or polypyrrole. In some embodiments, the composition includes the first component and the third component but not the second component. For example, in one embodiment, the composition includes ammonium molybdate and pyrrole but not graphene oxide or reduced graphene oxide.

Figure 2A:
FIG. 2A is a diagram of a one-layer composition for phosphate sensing, in accordance with some embodiments.

In some embodiments, as illustrated in FIG. 2A, the composition is in the form of a first layer 205 in which the first component, the second component, and the third component are homogenously dispersed in the first layer 205.

Figure 2B:
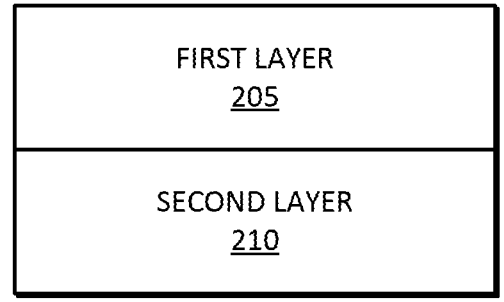
FIG. 2B is a diagram of a two-layer composition for phosphate sensing, in accordance with some embodiments.

In some embodiments, as illustrated in FIG. 2B, the first and third components of the composition is in the form of a first layer 205 and the second component of the composition is in the form of second layer 210 that is electrically connected to the first layer 205. The first and third components of the composition are homogenously dispersed in the first layer 205. In some embodiments, the first layer 205 is essentially free of the second component of the composition and the second layer 210 is essentially free of the first and third components of the composition.

Figure 2C:
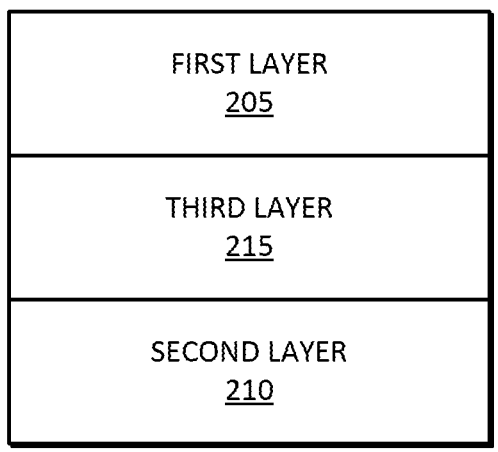
FIG. 2C is a diagram of a three-layer composition for phosphate sensing, in accordance with some embodiments.

In some embodiments, as illustrated in FIG. 2C, the first component of the composition is in the form of a first layer 205, the second component of the composition is in the form of second layer 210, and the third component of the compositions is in the form of a third layer 215. The third layer 215 is electrically connected to the first layer 205 and the second layer 210. In addition, the third layer 215 is located between the first layer 205 and the second layer 210, as illustrated in FIG. 2C. In some embodiments, the first layer 205 is essentially free of the second and third components of the composition, the second layer 210 is essentially free of the first and third components of the composition, and the third layer 215 is essentially free of the first and second components of the composition.

Figure 3A:
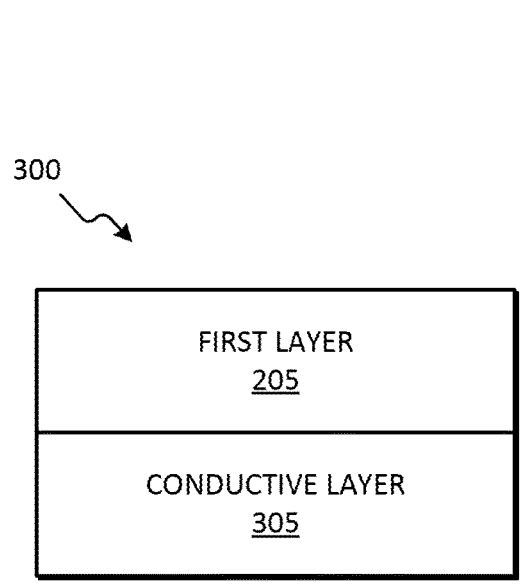
FIG. 3A is a diagram of a two-layer electrode for phosphate sensing, in accordance with some embodiments.

FIG. 3A is a diagram of one example embodiment of an electrode 300 for phosphate sensing that includes a conductive layer 305 and the first layer 205. In some embodiments, the conductive layer 305 includes carbon (for example, graphite). In some embodiments, the first layer 205 includes the first component of the composition and is essentially free of the second and third components of the composition. Alternatively or in addition, the first layer 205 includes a homogeneous mixture of the first and third components of the composition and is essentially free of the second component of the composition. Alternatively or in addition, the first layer 205 includes a homogeneous mixture of the first, second, and third components of the composition.

Figure 3B:
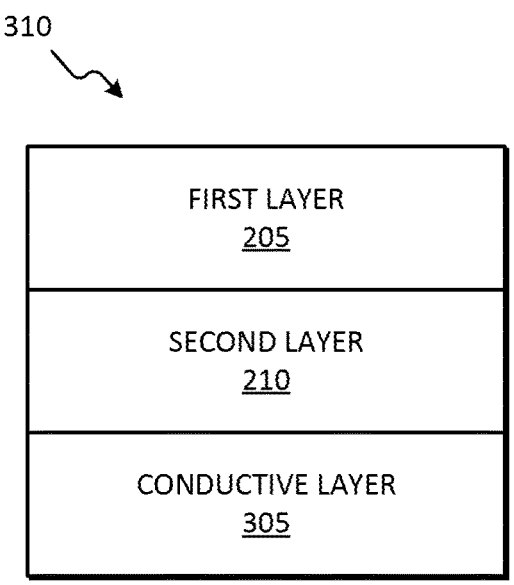
FIG. 3B is a diagram of a three-layer electrode for phosphate sensing, in accordance with some embodiments.

FIG. 3B is a diagram of another example embodiment of an electrode 310 for phosphate sensing that includes the conductive layer 305, the first layer 205, and the second layer 210. The second layer 210 is electrically connected to the conductive layer 305 and the first layer 205. The second layer 210 is located between the conductive layer 305 and the first layer 205. In some embodiments, the conductive layer 305 includes carbon (for example, graphite). In some embodiments, the first layer 205 includes the first and third components of the composition and the second layer 210 includes the second component of the composition. For example, in one embodiment, the first layer 205 includes a homogenous mixture of the ammonium molybdate and pyrrole and the second layer 210 includes graphene oxide. In some embodiments, the first layer 205 is essentially free of the second component of the composition and the second layer 210 is essentially free of the first and third components of the composition.

Figure 3C:
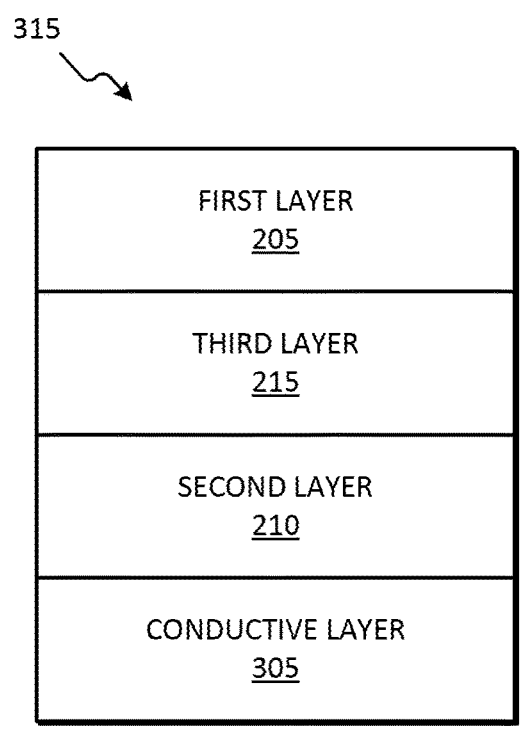
FIG. 3C is a diagram of a four-layer electrode for phosphate sensing, in accordance with some embodiments.

FIG. 3C is a diagram of another example embodiment of an electrode 315 for phosphate sensing that includes the conductive layer 305, the first layer 205, the second layer 210, and the third layer 215. The second layer 210 is electrically connected to the conductive layer 305 and the third layer 215. The second layer 210 is located between the conductive layer 305 and the third layer 320. The third layer 215 is electrically connected to the first layer 205 and the second layer 210. The third layer 215 is located between the first layer 205 and the second layer 210. In some embodiments, the conductive layer 305 includes carbon (for example, graphite). In some embodiments, the first layer 205 includes the first component of the composition, the second layer 210 includes the second component of the composition, and the third layer 215 includes the third component of the composition. For example, in one embodiment, the first layer 205 includes ammonium molybdate, the second layer 210 includes reduced graphene oxide, and the third layer 215 includes polypyrrole. In some embodiments, the first layer 205 is essentially free of the second and third components of the composition, the second layer 210 is essentially free of the first and third components of the composition, and the third layer 215 is essentially free of the first and second components of the composition.

In some embodiments, the conductive layer 305 is (or is part of) the working electrode 125 of the screen-printed electrode 105. In such embodiments, the conductive layer 305 includes (or is) a conductive surface of the working electrode 125.

Figure 4A:
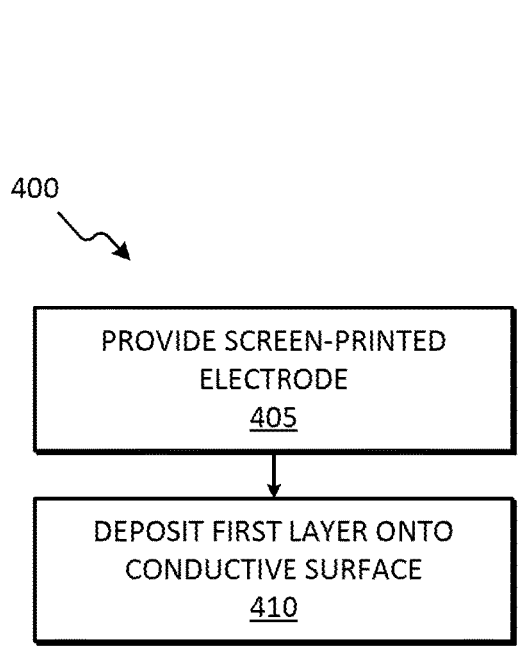
FIG. 4A is a flowchart of a method for fabricating the two-layer electrode of FIG. 3A, in accordance with some embodiments.

As described herein, in some embodiments, one layer is deposited onto the conductive surface of the working electrode 125, as illustrated in FIG. 3A. FIG. 4A illustrates an example method 400 for fabricating a two-layer electrode for phosphate sensing. The method 400 is described with respect to the components illustrated in FIGS. 1 and 3A. However, it should be understood that in some embodiments, all or portions of the method 400 may be used with other components. At block 405, the screen-printed electrode 105 is provided. The screen-printed electrode 105 includes, among other things, the working electrode 125. The working electrode 125 includes a conductive surface (for example, conductive layer 305 in FIG. 3A). At block 410, the first layer 205 is deposited onto the conductive surface (for example, via drop-casting or electro-polymerization). For example, the first layer 205 is deposited onto the conductive layer 305. The first layer 205 includes a first component selected from a group consisting of cobalt oxide nanoparticle, tin (IV) chloride, diphenyltin dichloride, and ammonium molybdate. In some embodiments, the first layer 205 further includes pyrrole or polypyrrole. In some embodiments, the first layer 205 includes ammonium molybdate and pyrrole.

Figure 4B:
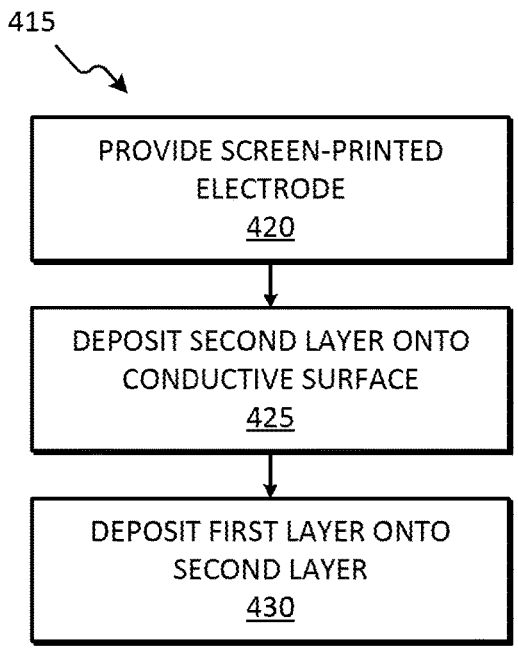
FIG. 4B is a flowchart of a method for fabricating the three-layer electrode of FIG. 3B, in accordance with some embodiments.

As described herein, in some embodiments, two layers are deposited onto the conductive surface of the working electrode 125, as illustrated in FIG. 3B. FIG. 4B illustrates an example method 415 for fabricating a three-layer electrode for phosphate sensing. The method 415 is described with respect to the components illustrated in FIGS. 1 and 3B. However, it should be understood that in some embodiments, all or portions of the method 415 may be used with other components. At block 420, the screen-printed electrode 105 is provided. The screen-printed electrode 105 includes, among other things, the working electrode 125. The working electrode 125 includes a conductive surface (for example, conductive layer 305 in FIG. 3B). At block 425, the second layer 210 is deposited onto the conductive surface (for example, via drop-casting or electro-polymerization). For example, the second layer 210 is deposited onto the conductive layer 305. The second layer 210 includes a second component. The second component is either graphene oxide or reduced graphene oxide. At block 430, the first layer 205 is deposited onto the second layer 210 (for example, via drop-casting or electro-polymerization). The first layer 205 includes a first component and a third component. The first component is selected from a group consisting of cobalt oxide nanoparticle, tin (IV) chloride, diphenyltin dichloride, and ammonium molybdate. The third component is either pyrrole or polypyrrole. In some embodiments, the first layer 205 includes ammonium molybdate and pyrrole, and the second layer 210 includes graphene oxide.

Figure 4C:
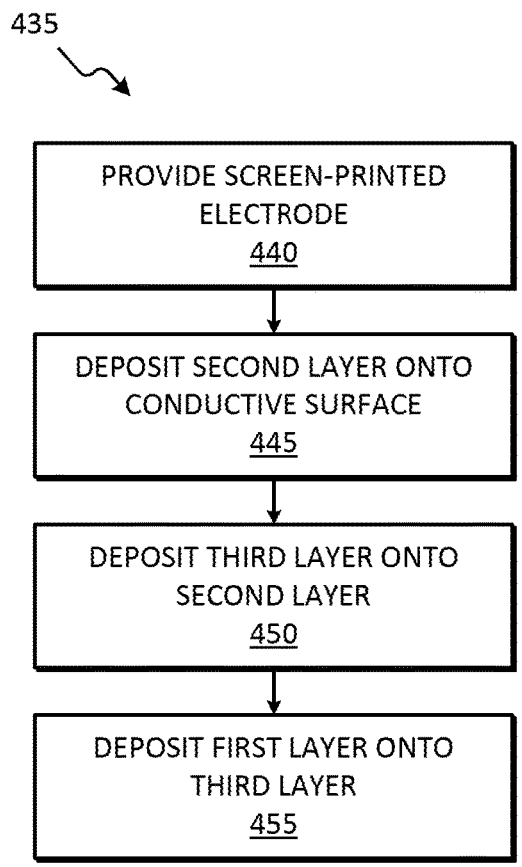
FIG. 4C is a flowchart of a method for fabricating the four-layer electrode of FIG. 3C, in accordance with some embodiments.

As described herein, in some embodiments, three layers are deposited onto the conductive surface of the working electrode 125, as illustrated in FIG. 3C. FIG. 4C illustrates an example method 435 for fabricating a four-layer electrode for phosphate sensing. The method 435 is described with respect to the components illustrated in FIGS. 1 and 3C. However, it should be understood that in some embodiments, all or portions of the method 435 may be used with other components. At block 440, the screen-printed electrode 105 is provided that includes the working electrode 125. The working electrode 125 includes a conductive surface (for example, conductive layer 305 in FIG. 3C). At block 445, the second layer 210 is deposited onto the conductive surface (for example, via drop-casting or electro-polymerization). For example, the second layer 210 is deposited onto the conductive layer 305. The second layer 210 includes a second component. The second component is either graphene oxide or reduced graphene oxide. At block 450, the third layer 215 is deposited onto the second layer 210 (for example, via drop-casting or electro-polymerization). The third layer 215 includes a third component. The third component is either pyrrole or polypyrrole. At block 455, the first layer 205 is deposited onto the third layer 215 (for example, via drop-casting or electro-polymerization). The first layer 205 includes a first component. The first component is selected from a group consisting of cobalt oxide nanoparticle, tin (IV) chloride, diphenyltin dichloride, and ammonium molybdate. In some embodiments, the first layer 205 includes ammonium molybdate, the second layer 210 includes reduced graphene oxide, and the third layer 215 includes polypyrrole.

EXAMPLES

Example 1. General Methods

Chemicals and materials: Standard phosphate solutions with different concentrations were prepared using potassium dihydrogen phosphate (KH2PO4) purchased from EMD Millipore. The pH of phosphate (H2PO4-) in aqueous solution with DI water was pH 4.5. Graphene Oxide water dispersion ([4 mg/mL, >95%]) was purchased from Graphenea Inc. All the other chemicals and reagents including; Acetone (ACS reagent, ≥99.5%), Potassium Chloride (reagent grade, 98%), Pyrrole (reagent grade, 98%), Sulfuric acid, Sodium Chloride, Cobalt Oxide powder (99.5%, <50 nm), Tin (IV) Chloride (99.995% trace metals basis), Diphenyltin Dichloride (96%), and Ammonium Molybdate Tetrahydrate (BioReagent, 81.0-83.0% MoO3 basis) used in this experiment were analytical grade purchased from Sigma-Aldrich. The Cl— ion in Potassium Chloride (1.0 M) was selected as an interfering molecule of phosphate sensing. All solutions were prepared with deionized water. An off-the-shelf screen-printed electrode (SPE) from eDAQ Pty Ltd was used. Three electrodes of the SPE are a graphitic carbon electrode as working electrode (central circle, diameter=3 mm), a graphitic carbon electrode (outer annular crescent) as counter electrode, and an Ag/AgCl electrode as reference electrode. All electrochemical measurements were performed using CHI-6012E, a computer-controlled electrochemical analyzer (CHI Co.) at room temperature. The Scanning Electron Microscope (SEM) images were taken using the JEOL JSM-6460 LV with Energy Dispersive Spectroscopy and the Plasma Sputter Coating equipment in Advanced Analysis Facility (AAF) at the College of Engineering and Applied Science, University of Wisconsin-Milwaukee.

Sensor electrode cleaning: All the new bare SPE sensors were cleaned before the surface modification of the working electrode. The new SPE was cleaned with 0.1 M H2SO4 solution by cyclic voltammetry (0.0 to 1.4 V, 15 cycles, scan rate 50 mV/s), followed by soaking (only the electrode portion) in 0.1 M NaCl solution and then acetone for 1 minute each to remove any physically adsorbed materials on the surface of the electrodes. The SPE was cleaned in fresh DI water between each cleaning step using squeeze wash bottle. After cleaning, all the sensors were dried at room temperature for 8 hours before treatment.

Modifications of working electrode surface: Graphene oxide/pyrrole (GO/Py) nanocomposite offers large surface area, fast electron transfer rate, increased mass transport rate, enhanced electro-catalytic properties, lower solution resistance, and higher signal-to-noise ratio. For better sensitivity and selectivity, GO and Py were mixed with the other compounds and used as layers or mixtures for surface treatment of the working electrode.

Several combinations of GO/Py were tried to determine the optimum combination for phosphate detection. A homogeneous mixture of Graphene Oxide, pyrrole (monomer) and a third compound (cobalt oxide nanoparticles, tin (IV) chloride, diphenyltin dichloride or ammonium molybdate) were used for surface treatment of the SPE electrode according to the following combinations.

- Homogeneous mixture of graphene oxide, pyrrole, and one of the third compounds
- Homogeneous mixture of pyrrole and one of the third compounds
- A layer of graphene oxide and a layer of one of the third compounds
- A layer of pyrrole and a layer of one of the third compounds
- A layer of reduced graphene oxide and a layer of homogeneous mixture of pyrrole and one of the third compounds
- A layer of graphene oxide, a layer of pyrrole and a layer of one of the third compounds
- A layer of reduced graphene oxide, a layer of polpyrrole and a layer of one of the third compounds Individual layers or mixtures of GO, Py and cobalt oxide nanoparticles, tin (IV) chloride, diphenyltin dichloride or ammonium molybdate were drop-casted on the working electrode of the SPE sensor. GO was effectively reduced to rGO through in-situ electrochemical reduction method using cyclic voltammetry (CV) with N2 purged pH 5.0 phosphate buffered saline (PBS buffer) with potential range from 0.0 V to 1.4 V, scan rate of 50 mV/s for 15 complete cycles. PPy was grown on the working electrode surface using cyclic voltammetry with 0.1 M Py solution for potential range from −0.2 to 1.2 V with scan rate of 100 mV/s for 5 complete cycles. The modified SPE sensors were dried for 24 hours at room temperature between applications of each layer. Different concentrations of the cobalt nanoparticles, tin (IV) chloride, diphenyltin dichloride, and ammonium molybdate solutions were prepared by ultrasonicating the reagents for 6 hours. The mixtures of the nanomaterials and chemicals were dissolved by mixing with magnetic stirrer for 60 min.

Figure 5:
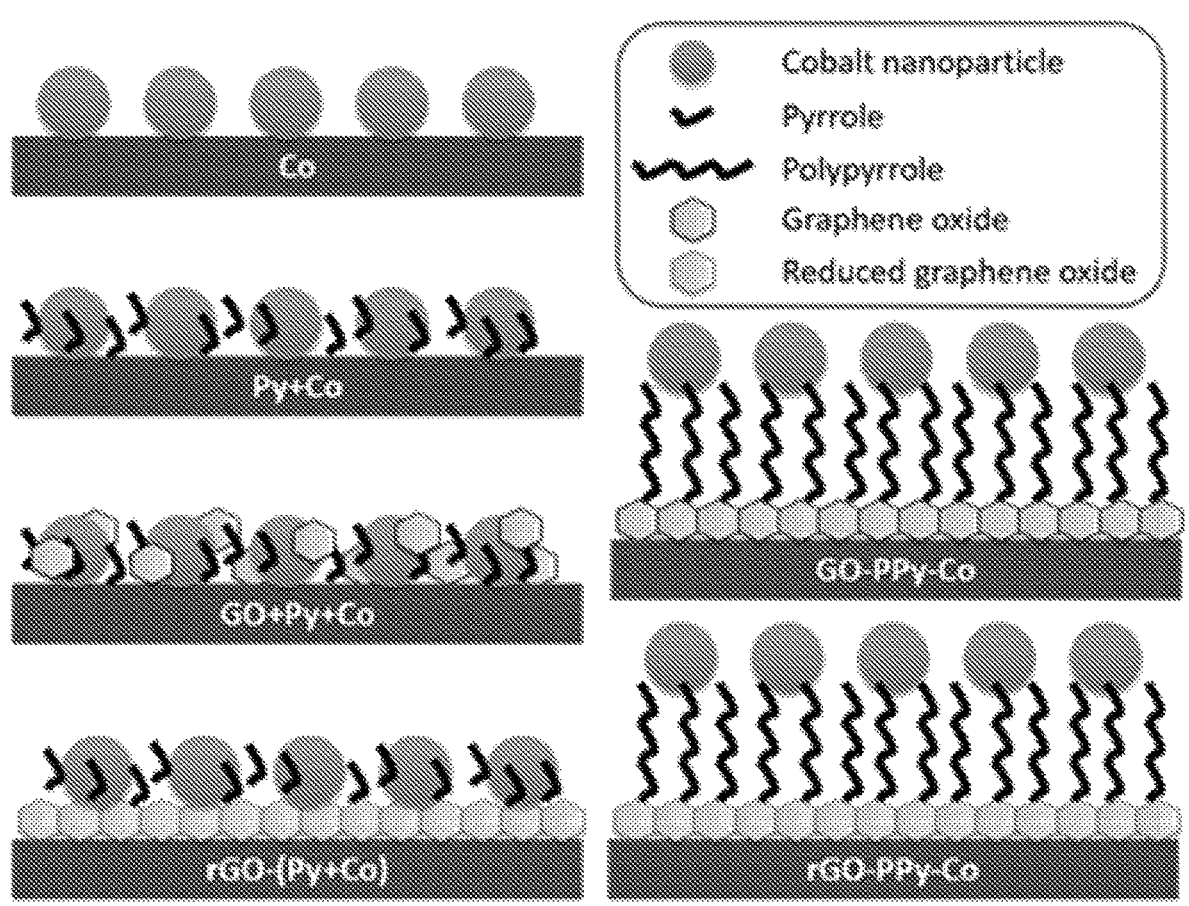
FIG. 5 is a schematic of sensor structures with different combinations (layers and mixtures) of cobalt oxide nanoparticles, graphene oxide, and pyrrole, in accordance with some embodiments.

Cobalt oxide nanoparticle treatment: As a control layer, wide ranges (1.5-15 mg/mL) of cobalt oxide nanoparticle solutions were tested to modify the working electrode of the SPE. FIG. 5 shows the schematic of the sensor structure with cobalt oxide nanoparticles. An 8 µL aliquot of the different concentration solutions were drop casted on the working electrode and dried at room temperature for 24 hours to modify the surface of the working electrode. For better selectivity and sensitivity, a total 4 different configurations of GO, Py and cobalt oxide nanoparticles were tested. (1) A homogeneous mixture of 3 mg/mL GO, 0.3 M Py and cobalt oxide nanoparticle solution was tested. A total of five different concentrations of cobalt oxide nanoparticle solutions were used, and the same volume of each solution was mixed. (2) A homogeneous mixture of 0.2 M Py and 6 mg/mL cobalt oxide solution was mixed with the same ratio and deposited. GO was not included in this configuration. (3) 3 separate layers of 1 mg/mL GO, 0.1 M PPy, and cobalt oxide nanoparticles, respectively, were prepared. The first GO layer was drop casted using 8 µL of 1 mg/mL GO solution, followed by drying at room temperature for 24 hours. Then, a thin film of PPy (0.1 M) was grown on top of GO layer using cyclic voltammetry. Finally, an 8 µL aliquot of a cobalt oxide nanoparticle solution (3 mg/mL) was drop-casted as a third layer on the working electrode surface. (4) A very similar method was applied with the reduced graphene oxide. An about 8 µL aliquot of the homogeneous mixture (same ratio) of Pyrrole-Cobalt oxide nanoparticles was drop-casted and dried at room temperature for 24 hours after formation of rGo layer on the surface of the working electrode.

Optimized concentrations of graphene oxide, pyrrole, and cobalt oxide nanoparticles were 1 mg/mL, 0.2 M and 6 mg/mL respectively. For the reduced graphene oxide-pyrrole-cobalt oxide layers, the optimum concentrations of graphene oxide, pyrrole and cobalt oxide nanoparticles were 1 mg/mL, 0.1 M and 3 mg/mL, respectively.

Figure 6:
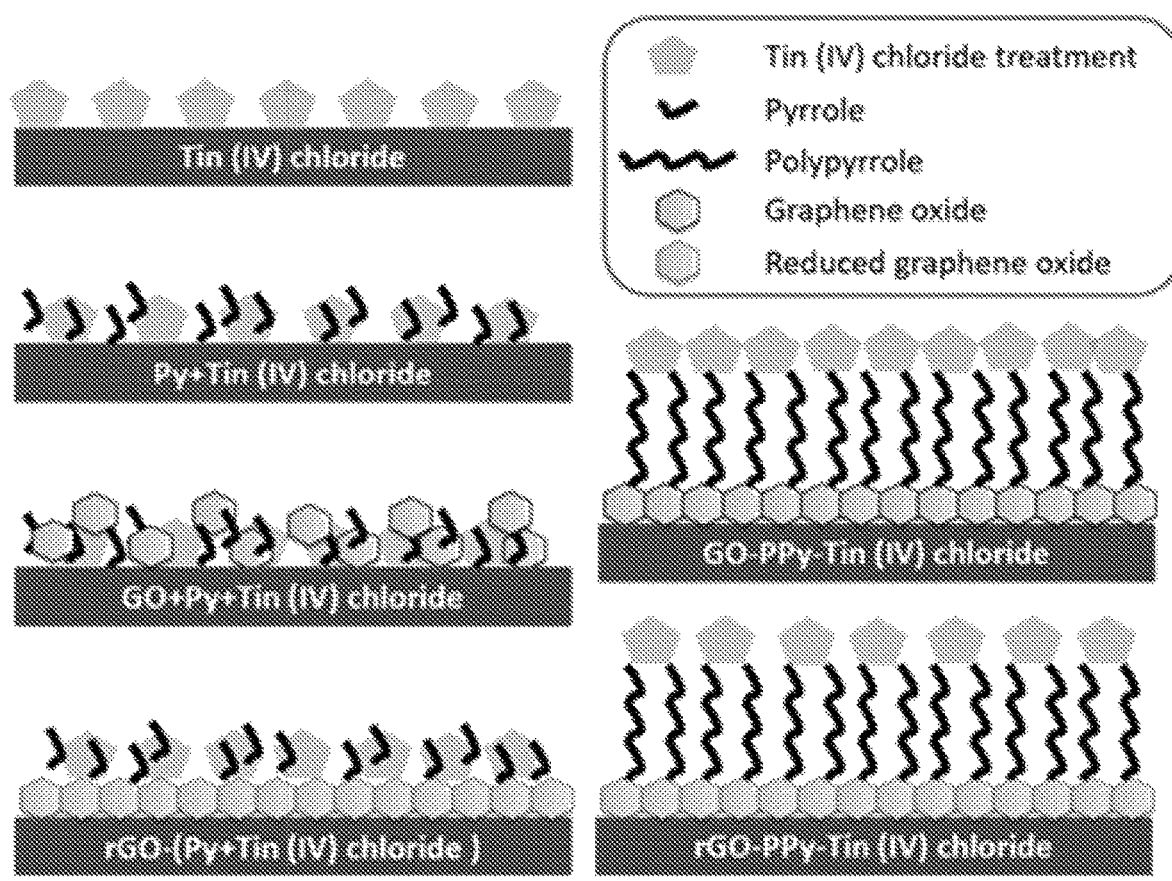
FIG. 6 is a schematic of sensor structures with different combinations (layers and mixtures) of tin (IV) chloride, graphene oxide, and pyrrole, in accordance with some embodiments.
Figure 7:
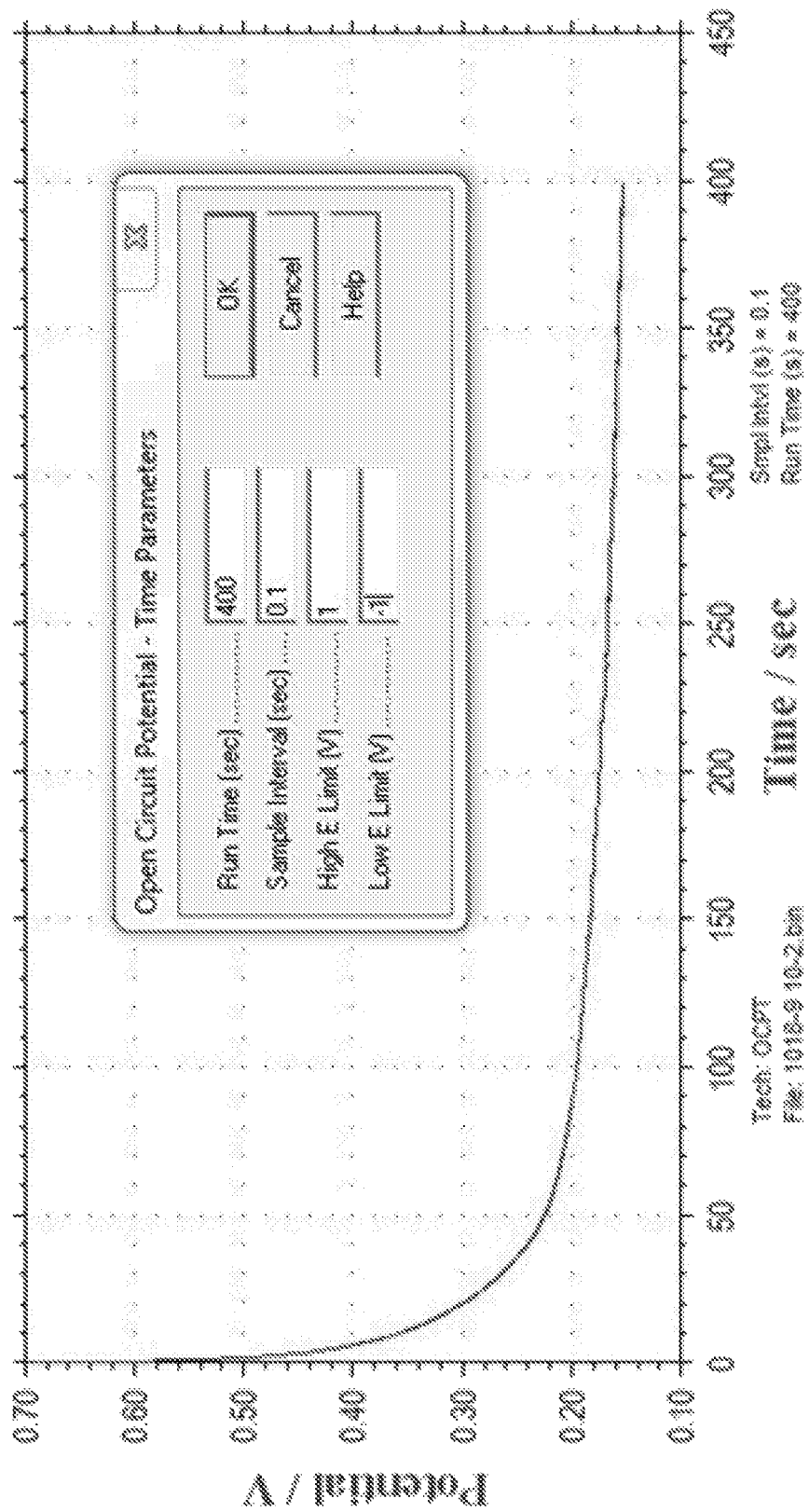
FIG. 7 is a graph of an open circuit potential test (OCPT) readings of a single measurement with a phosphate sensor modified with cobalt oxide nanoparticles, in accordance with some embodiments.

Tin (IV) chloride treatment: FIG. 6 shows the side view schematic of the sensor structure modified with tin (IV) chloride. Several concentrations of tin (IV) chloride were prepared with DI water. First, an aliquot of 8 µL of tin (IV) chloride was drop casted on the working electrode and dried at room temperature for 24 hours. For better sensitivity, GO and Py were combined with tin (IV) chloride similar to the nanoparticles mentioned above. The optimum concentration of tin (IV) chloride was experimentally determined to be $10^{-3}$ M based on the lower detection limit. Seven different combinations were tried with tin (IV) Chloride. (1) A mixture of GO, Py and tin (IV) chloride was prepared by mixing equal volumes of 3 g/L GO, 0.3 M Py, and $3×10^{-3}$ M tin (IV) chloride solution. The mixture solution was drop casted on the working electrode and dried at room temperature for 24 hours. (2) A mixture of 0.2 M pyrrole and $2×10^{-3}$ M tin (IV) chloride was prepared and then an 8 µL aliquot was drop-casted on the working electrode. (3) An aliquot of 8 µL of GO 1 mg/mL was drop-casted and dried at the room temperature for 24 hours. After that, tin (IV) chloride $10^{-3}$ M was drop-casted on top of GO layer. (4) A thin film of PPy (0.1 M) was grown on top of the sensor electrode using cyclic voltammetry technique and then tin (IV) chloride of $10^{-3}$ M was drop-casted on top of the PPy layer. (5) An 8 µL aliquot of GO (1 mg/mL) was drop-casted and dried at room temperature. After that, a thin film of PPy (0.1 M) was grown using cyclic voltammetry technique on top of the GO layer. Then, 8 µL of tin (IV) chloride ($10^{-3}$ M) was drop casted as a third layer on top of PPy layer. (6) A GO (1 mg/mL) layer was electrochemically reduced into rGO after drop casting. After that, a thin film of PPy (0.1 M) was grown using cyclic voltammetry technique on top of the GO layer. Then, 8 µL of tin (IV) chloride ($10^{-3}$ M) was drop casted as a third layer on top of PPy layer. (7) A GO (1 mg/mL) layer was electrochemically reduced into rGO after drop casting. Then, an aliquot of 6 µL of homogenous mixture of Py (0.2 M) and tin (IV) chloride ($10^{-3}$ M) was drop casted and dried at room temperature.

Diphenyltin Dichloride Treatment: Diphenyltin dichloride was dissolved in ethanol and a 6 µL aliquot was drop-casted on the working electrode and dried at room temperature for 24 hours. Five different combinations were tried with diphenyltin dichloride. (1) A 6 µL aliquot of a homogeneous mixture of 3 mg/L GO, 0.3 M Py and 0.3 M diphenyltin dichloride was drop-casted on the working electrode surface and dried at room temperature. (2) An approximate 8 µL aliquot of a homogeneous mixture of 0.2 M Py and 0.2 M diphenyltin dichloride was drop casted on the working electrode and dried at room temperature for 24 hours. (3) An approximate 8 µL aliquot of 1 mg/mL GO, 0.1 M Py, and 0.1 M diphenyltin dichloride was drop casted in three different layers. Each of the layers was dried for 24 hours at room temperature. (4) An 8 µL aliquot of 1 mg/mL GO was drop casted and then electrochemically reduced. Then approximate 6 µL aliquots of each of 0.2 M Py and 0.2 M diphenyltin dichloride were drop-casted as two separate layers. All three layers were dried for 24 hours before drop casting of the next layer. (5) Total 8 µL of 1 mg/mL GO was drop casted and then reduced electrochemically. A mixture of 0.2 M Py and 0.2 M diphenyltin dichloride was drop-casted on top of the rGO layer.

Ammonium Molybdate Treatment: The optimum concentration of ammonium molybdate was determined as $10^{-3}$ M in DI water. An approximate 8 µL aliquot of ammonium molybdate was drop-casted on the working electrode and dried at room temperature for 24 hours. Five different combinations were tried with ammonium molybdate. (1) The homogenous mixture of 3 mg/mL GO, 0.3 M Py and $3×10^{-3}$ M ammonium molybdate was used to modify the working electrode of SPE sensor. The optimum concentrations of these elements were determined experimentally. The mixture was drop casted on the working electrode and dried at room temperature for 24 hours. (2) An approximate 8 µL aliquot of the mixture of 0.2 M Py and $2×10^{-3}$ M ammonium molybdate was drop-casted on the working electrode, and then dried at room temperature. (3) An 8 µL aliquot of 1 mg/mL GO was drop casted and dried at room temperature. Then, a thin film of PPy (0.1 M) was grown on top the GO layer using cyclic voltammetry technique. After that, an 8 µL aliquot of $10^{-3}$ M ammonium molybdate solution was drop casted as a third layer on top of the PPy layer. (4) An 8 µL aliquot of 1 mg/mL GO was drop casted and then reduced electrochemically. After that, a thin film of PPy (0.1 M) was grown on top the rGO layer using CV technique. And then, an 8 µL aliquot of a $10^{-3}$ M ammonium molybdate solution was drop casted as a third layer on top of the PPy layer. (5) An 8 µL aliquot of 1 mg/mL GO was drop casted and then reduced electrochemically. Then, a mixture of 0.2 M Py and $10^{-3}$ M ammonium molybdate solutions was drop casted on top of rGO layer.

In the fabrication processes for the screen-printed (SPE) phosphate sensor, both the polymerization and electrochemical reduction were carried out in a common three-electrode system. Pyrrole was used as monomer (for the drop casted model) and as a polymer (using the electrochemical polymerization process). All the fabricated sensors were washed with DI water (dip method) to remove any physically adsorbed nanocomposite film or loose particle before testing with the analytical solution.

Figure 31:
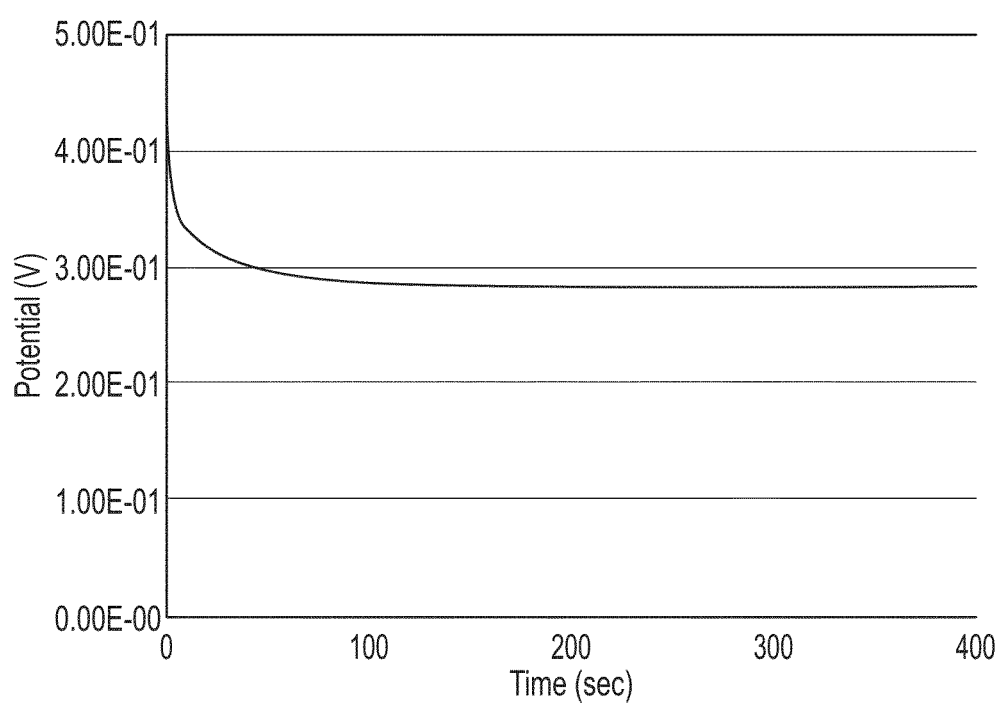
FIG. 31 is a graph illustrating phosphate sensing using open circuit voltammetry.

Open circuit voltammetry: Open circuit voltammetry was used to determine the concentration of phosphate in the sample solution. An exemplary graph of a single measurement is shown in FIG. 31. Using the three-electrode system the potential responses from the SPE phosphate sensor were recorded using the CHI-6012E electrochemical analyzer at room temperature. In open circuit voltammetry the potential is observed without any external current flowing in the system. The formation of phosphate complexes on the SPE sensor initiated a potential change after contacting H3PO4 solution.

For electrochemical detection of phosphate anions, various concentrations of H3PO4 were tested with the fabricated SPE sensor. The dipping method was used to test the developed phosphate sensor. The sensor was immersed in the sample solution for the open circuit time potential study. The testing was done for 400 sec and data was recorded with 0.1 sec interval at room temperature. A magnetic stirrer was used at about 750 rpm for a uniform phosphate concentration in the sample vial. The OCPT reading of a single measurement with a phosphate sensor modified with cobalt oxide nanoparticles is shown in FIG. 4. The concentration of cobalt oxide was 9 mg/mL and the concentration of phosphate was 10-4 M. The potential stabilizes between 200 to 300 s. Thus, the electrical potential of each phosphate concentration was determined by averaging the measured values from 300 to 400 s. The concentration ranges of phosphate ($H_2PO_4^-$) solutions of 10-11 M (mol/L) to 10-3 M (mol/L) were used to determine the sensitivity and lower detection limit of the developed sensor using open circuit voltammetry.

Interference Analysis: Using open circuit voltammetry as described above, phosphate concentration was measured in the presence of various concentrations of chloride anions. Chloride anion (Cl—) concentrations within the range from 5×10-4 M (mol/L) to 5×10-2 M (mol/L) were tested with the same concentrations of phosphate ions as those used to determine sensitivity.

Figure 8:
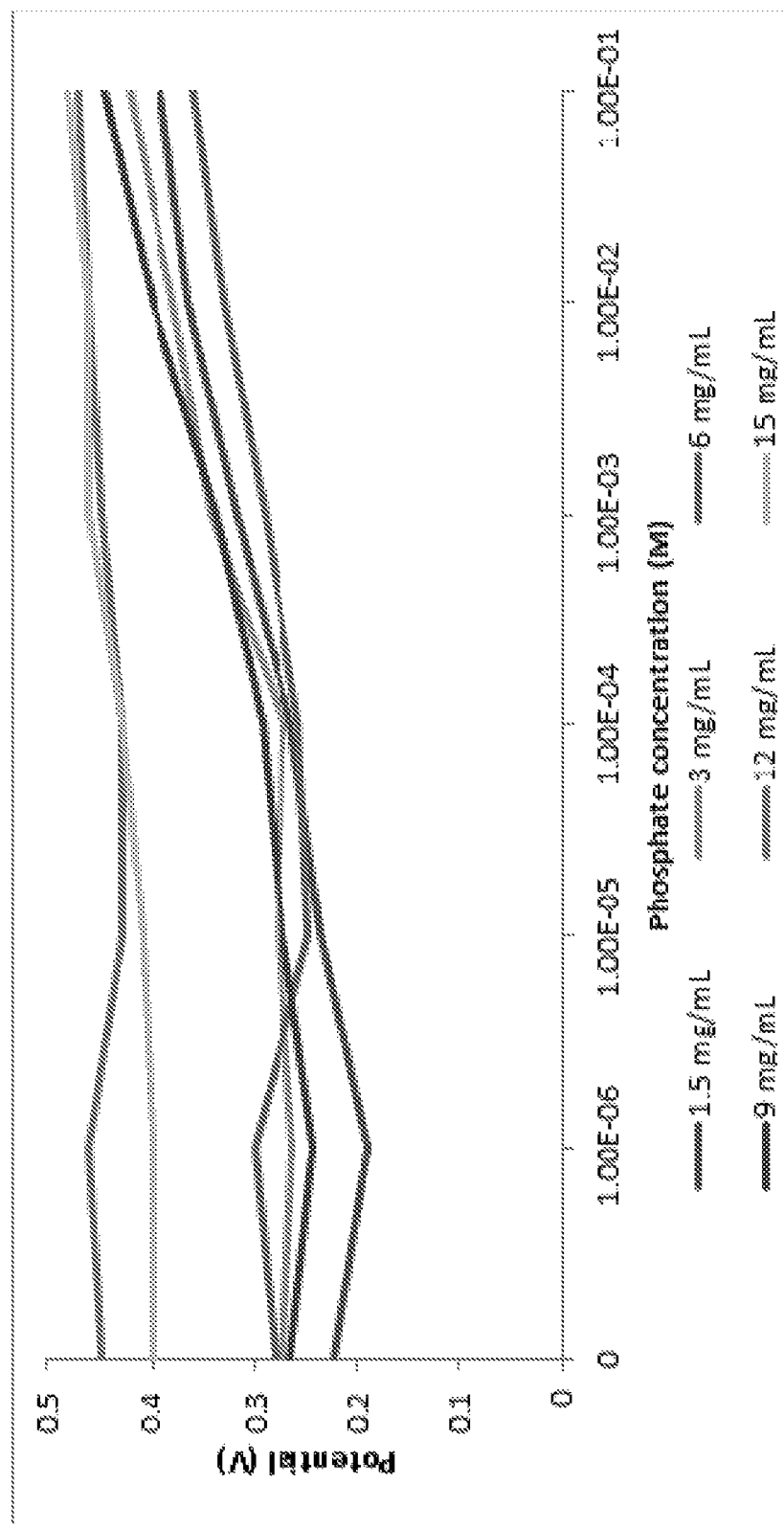
FIG. 8 is a graph illustrating phosphate detection using cobalt oxide nanoparticles in KH2PO4 in aqueous solution at pH 4.5.

Example 2. Cobalt Oxide Nanoparticle Effects on Phosphate Sensing with an SPE Sensor Cobalt Oxide Nanoparticles: To measure the effect of cobalt oxide on phosphate sensing cobalt oxide nanoparticles were drop casted on the working electrode and dried at room temperature. The measured potentials proportionally increased with higher concentrations of phosphate, as well as amount of cobalt nanoparticles. FIG. 8 shows the effect of concentration of cobalt oxide nanoparticles on phosphate sensing. The optimum concentration of Cobalt Oxide nanoparticles was determined to be 9 mg/mL with the lower detection limit of 10-6 M (mol/L), because 9 mg/ml showed highest slope among tested concentrations. Interestingly, cobalt nanoparticles concentrations higher than 9 mg/ml showed worse sensitivity.

Figure 9A:
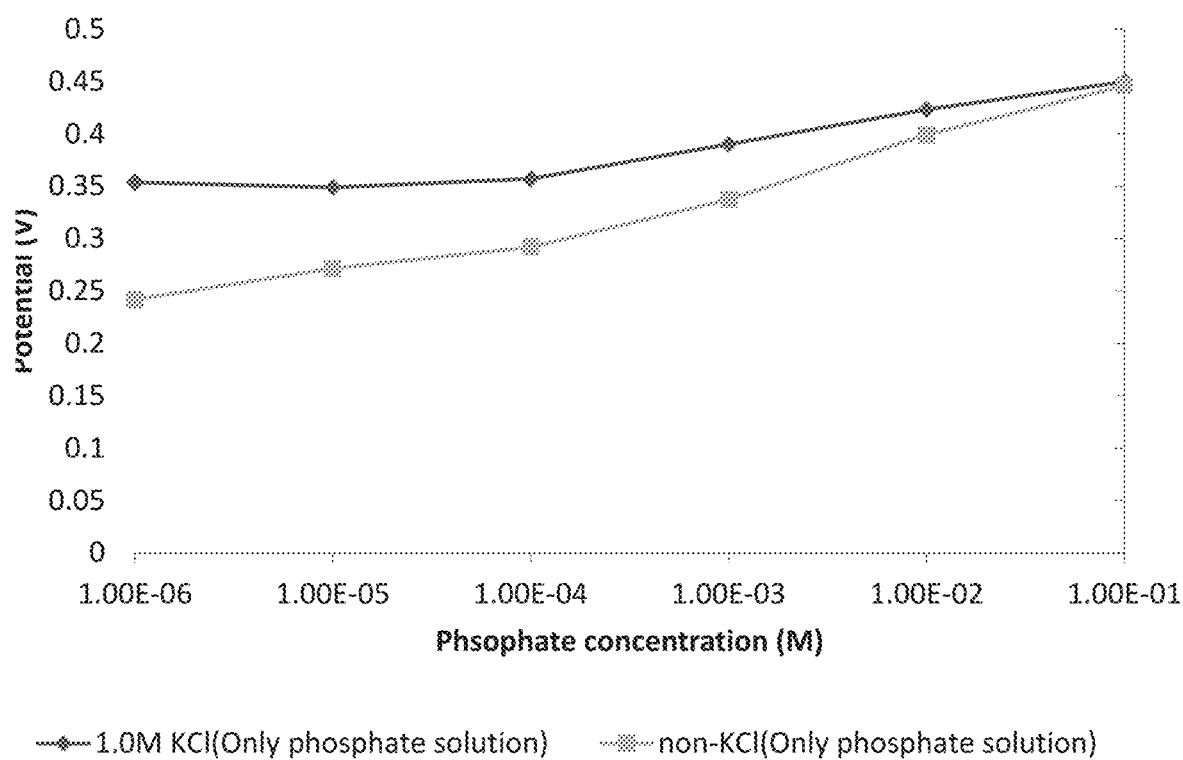
FIG. 9A and FIG. 9B illustrate an interference study of phosphate ions in presence of chloride ions using Cobalt oxide nanoparticles.
Figure 9B:
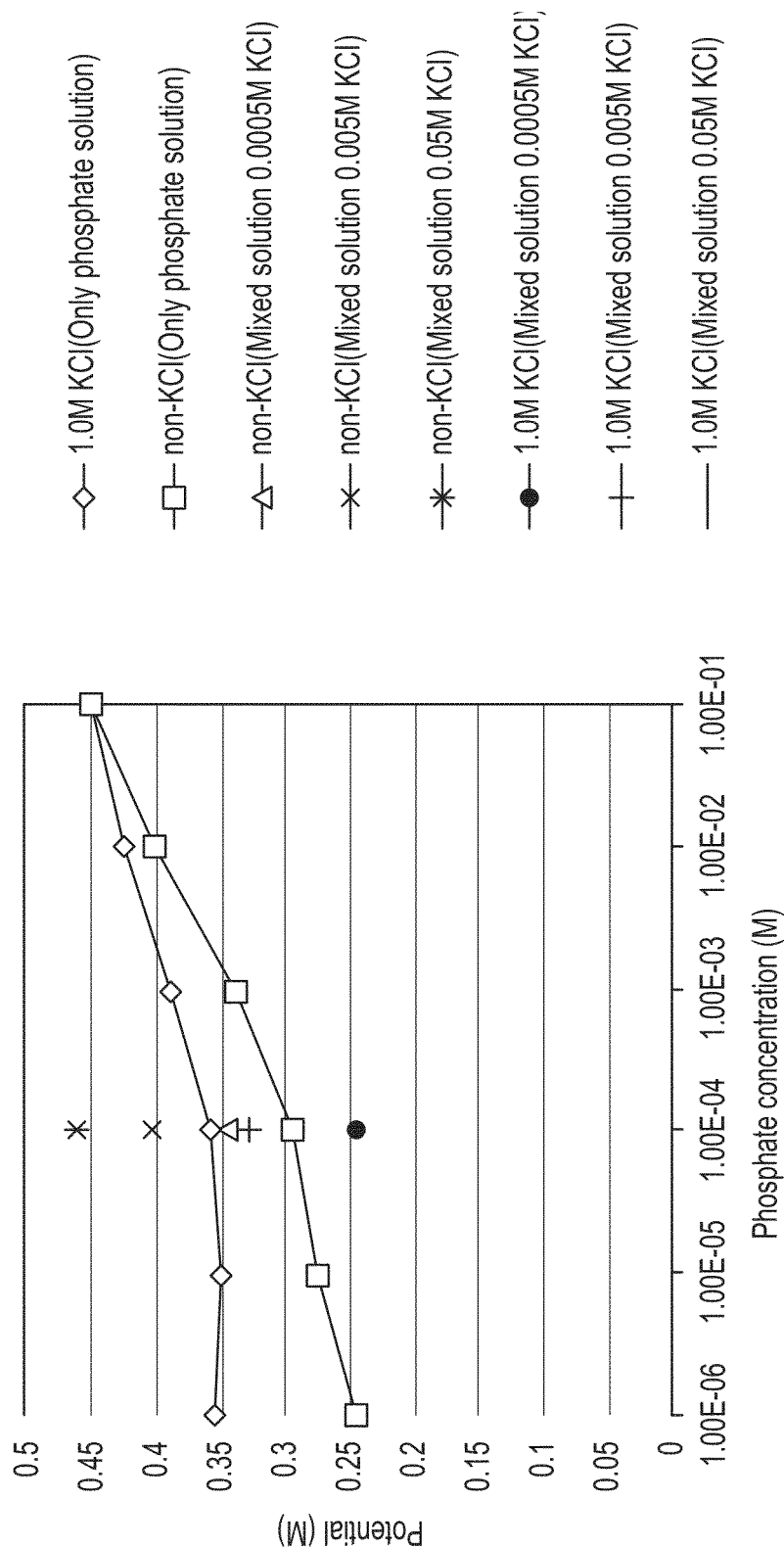
Figure 10A:
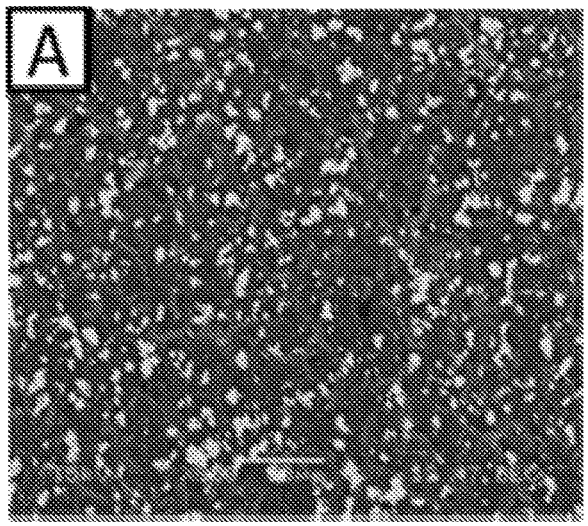
Figure 10B:
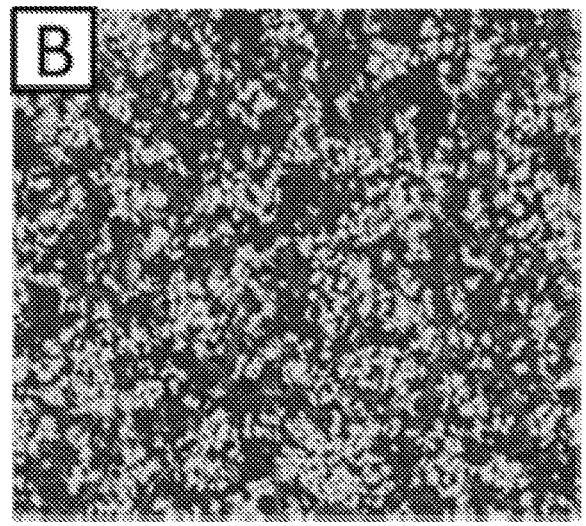
Figure 10C:
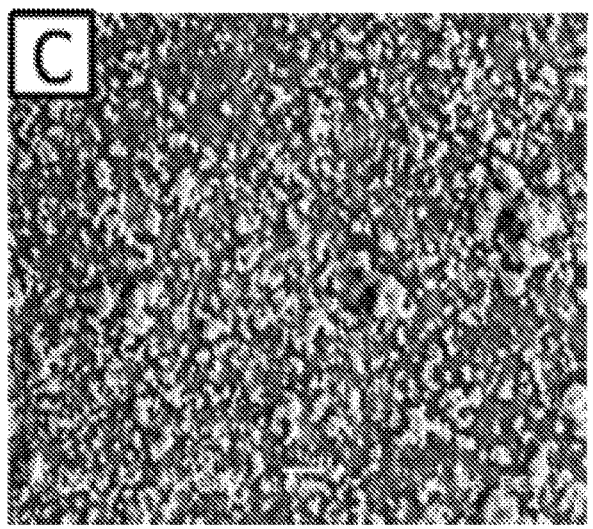
Figure 10D:
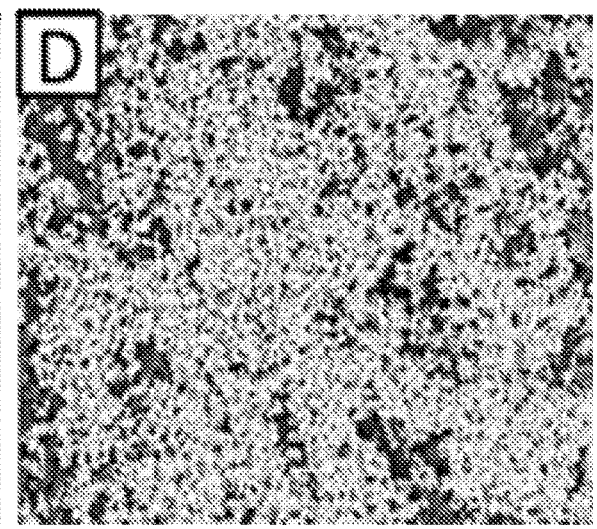

Also, the interference from KCl on the cobalt oxide phosphate sensor was investigated. KCl is a representative molecule to interfere the phosphate detection. KCl significantly increased the measured potential. It can be seen in FIG. 9A and FIG. 9B that at lower concentrations the signal from the phosphate solution showed a significant potential difference from the signal with the potassium chloride (1.0 M). The difference decreased with increasing phosphate concentration. Other measurements at various concentrations of KCl solution also indicated that cobalt oxide nanoparticle-treated surface was responding to KCl as well as phosphate, because the measured potential increased with increasing concentration of KCl. Due to the poor selectivity, the cobalt oxide nanoparticles may not be a reliable phosphate sensing system.

The scanning electron microscope (SEM) images in FIGS. 10A-10D show the amount of cobalt oxide nanoparticles deposited on the carbon electrode surface. Based on the amount of white particles displayed in the SEM images, 9 mg/ml (FIG. 10D) was determined as the optimum concentration of cobalt oxide nanoparticles to cover the surface in a dense layer.

Figure 11A:
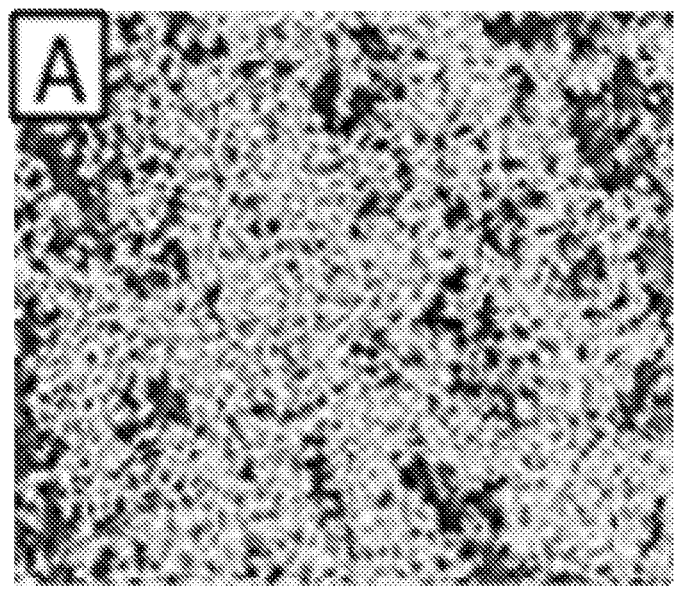
FIG. 11A and FIG. 11B are SEM images of the 9 mg/mL cobalt doped sensor surface before (FIG. 11A) and after (FIG. 11B) use.
Figure 11B:
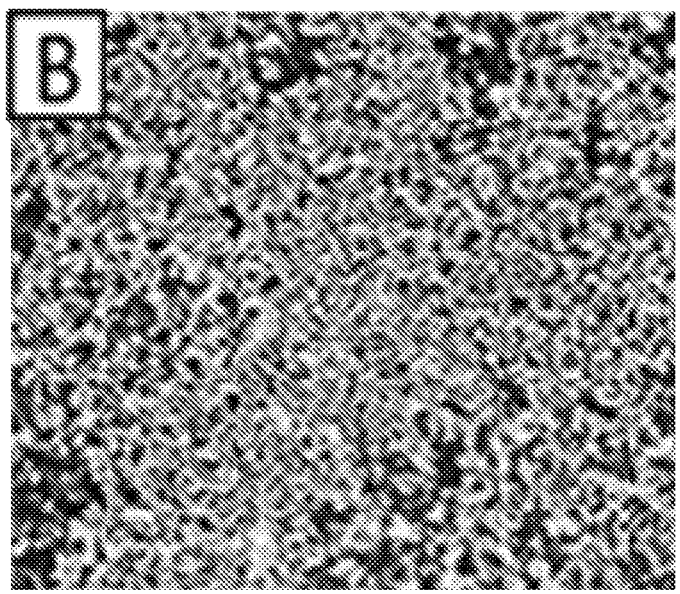

The morphology of the sensor surface was compared before and after use. This result can be used to estimate the robustness of the fabricated sensor. No significant effect was observed from the measurement on sensor surface morphology (see FIG. 11A and FIG. 11B).

Cobalt Oxide Nanoparticles with Graphene Oxide and Pyrrole: Though cobalt oxide nanoparticles reacted well with phosphate, there was significant interference from chloride anions, and the sensor sensitivity was similar to the conventionally used detection methods. For better selectivity and sensitivity, graphene oxide (GO) and pyrrole (Py) were combined with cobalt oxide nanoparticles. GO and Py nanocomposite has been shown to enhance the sensitivity and robustness of the sensor by offering large surface area, fast electron transfer rate, increased mass transport rate, enhanced electro-catalytic properties, lower solution resistance, and higher signal-to-noise ratio. Five different combinations of mixtures or layer-by-layer configurations were tested (see FIG. 12). Interestingly, mixtures of the components showed better responses than layer-by-layer configurations. Among the tested configurations, mixtures of cobalt nanoparticles with only pyrrole or with GO and pyrrole showed better responses to the phosphate (see FIG. 12).

Figure 12:
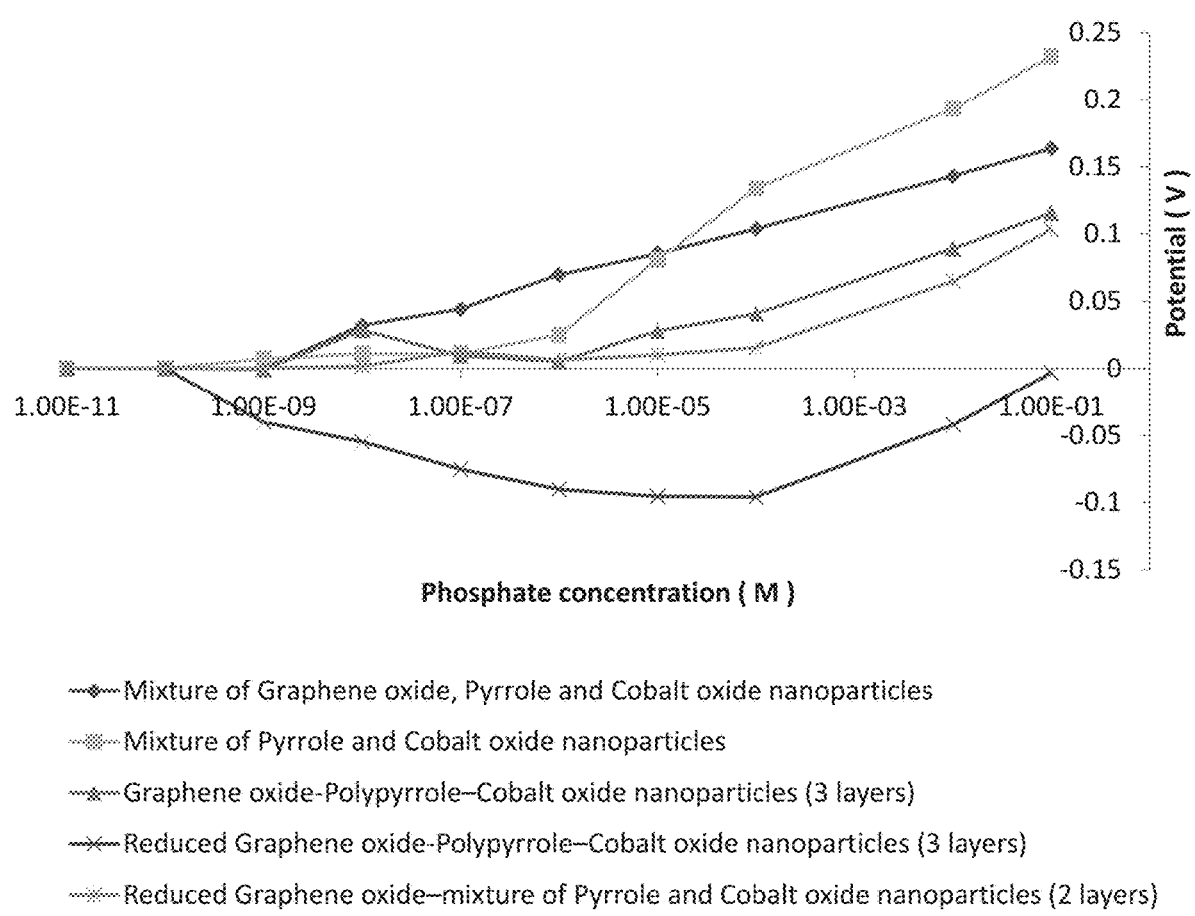
FIG. 12 is a graph illustrating phosphate detection using the cobalt oxide nanoparticle-graphene oxide-pyrrole combination in KH2PO4 aqueous solution at pH 4.5.
Figure 13A:
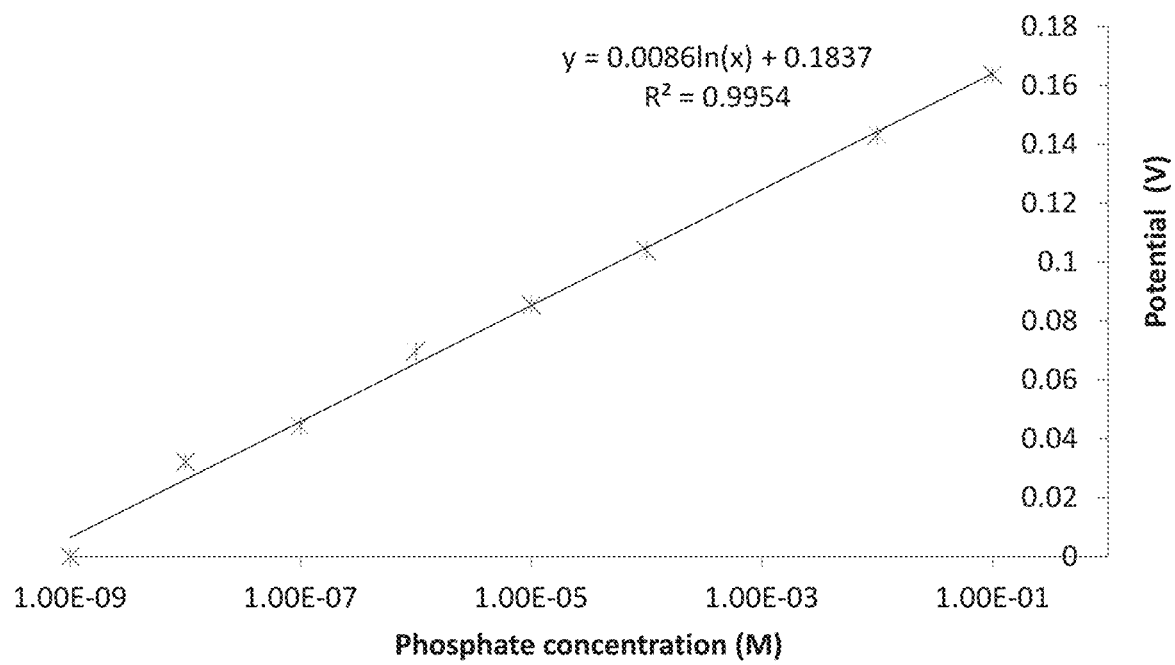
FIG. 13A and FIG. 13B are graphs illustrating phosphate detection (FIG. 13A) and an interference study (FIG. 13B) of phosphate ions in presence of Cl— ions using the mixture of graphene oxide, pyrrole and cobalt oxide nanoparticles in KH2PO4 in aqueous solution at pH 4.5.

The sensor fabricated with the nanoparticles from the homogeneous mixture of the GO, Py and cobalt oxide nanoparticles had the best sensitivity and linearity in respect to the concentration of phosphate ion (see FIG. 12). This combination was further studied, and the concentration of each individual nanomaterial was optimized; graphene oxide (3 mg/mL), pyrrole (0.3 M) and cobalt oxide nanoparticles (9 mg/mL). The lower detection limit was 10-9 M (mol/L). The average reading from the four different sensors (see FIG. 13A) showed a good linear trend on phosphate detection with $R^2$=0.9954. Use of a layer of a mixture of graphene oxide and pyrrole on the working electrode was not possible as the mixture became thicker/viscous over time.

Figure 13B:
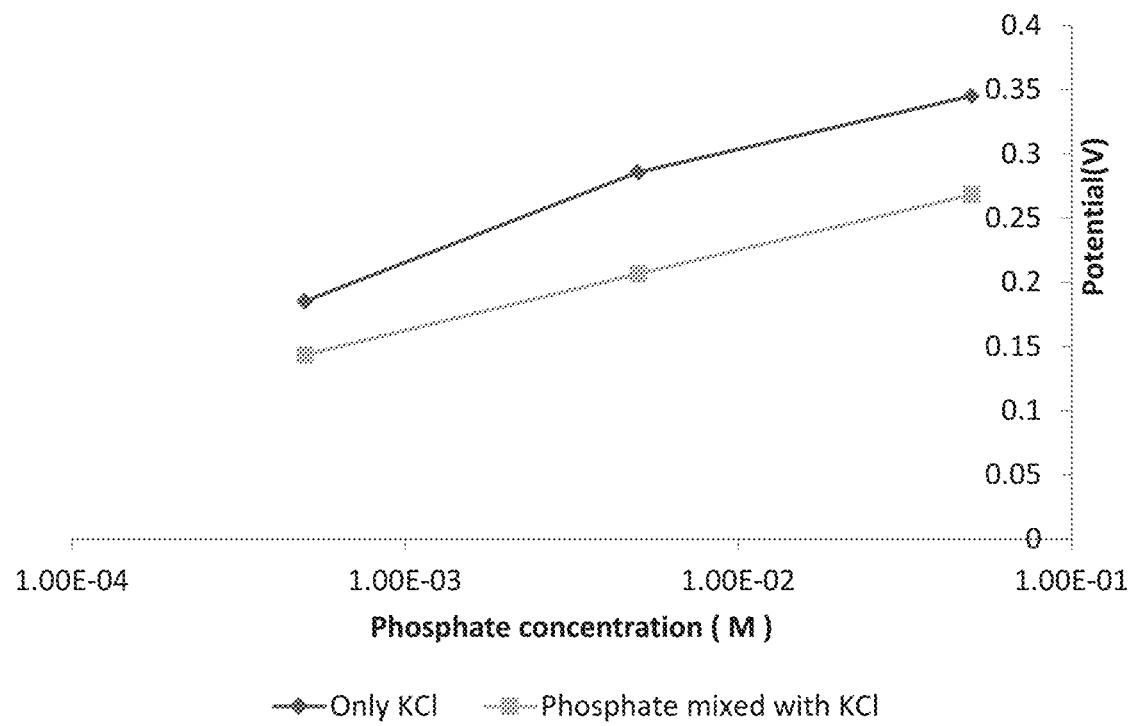
Figure 14A:
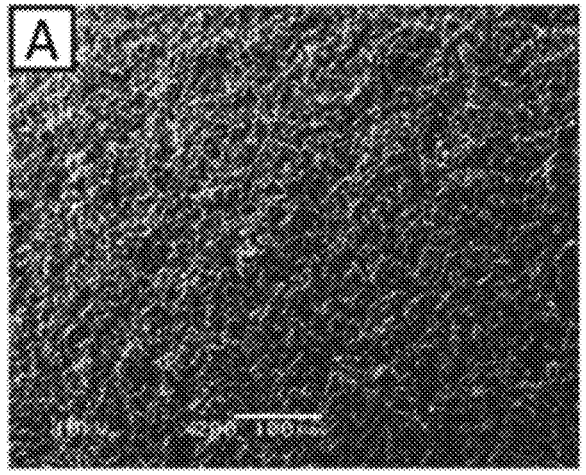
FIGS. 14A-14D are scanning electron microscopy (SEM) images of the mixture of graphene oxide, pyrrole and cobalt oxide nanoparticles before using ×200 magnification (FIG. 14A), before using ×1000 magnification (FIG. 14B), after using ×200 magnification (FIG. 14C) and after using ×1000 magnification (FIG. 14D).
Figure 14B:
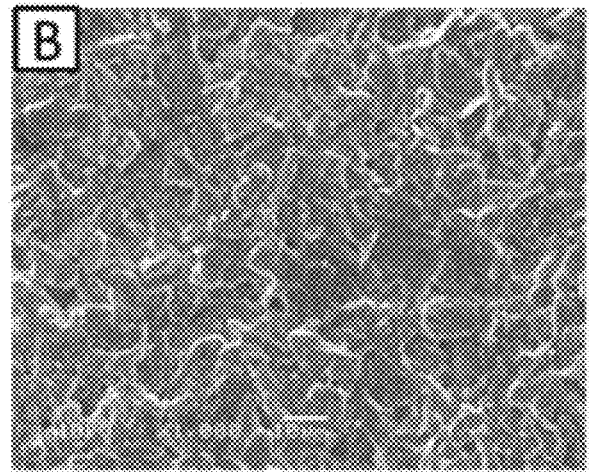
Figure 14C:
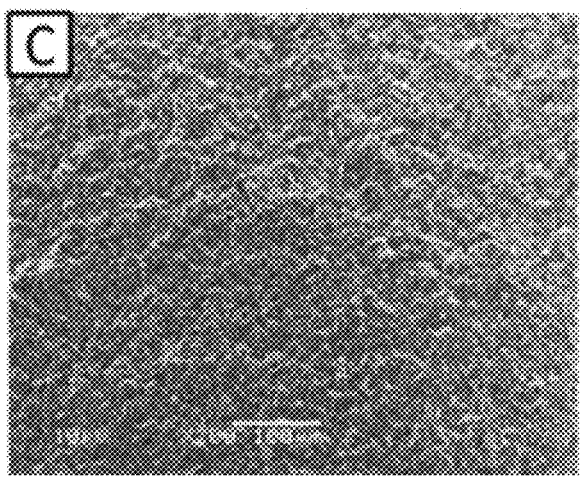
Figure 14D:
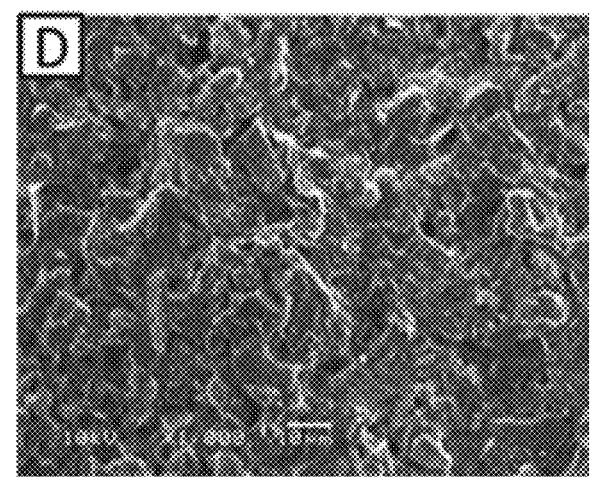

Comparison of potential difference with potassium chloride solution and phosphate mixed with potassium chloride solution is shown in FIG. 13B. The signal from the phosphate solution showed a significant potential difference from the signal with the potassium chloride (1.0 M). Since interference study is an important aspect of selectivity, the cobalt oxide nanoparticle treated sensor may not be a reliable system of phosphate detection.

The sensor modified with the mixture of graphene oxide, pyrrole, and cobalt oxide nanoparticles was imaged before and after using the sensor in phosphate detection. The presence of phosphate in the scanning electron microscope (SEM) images can be seen (see FIGS. 14A-14D).

Figure 15A:
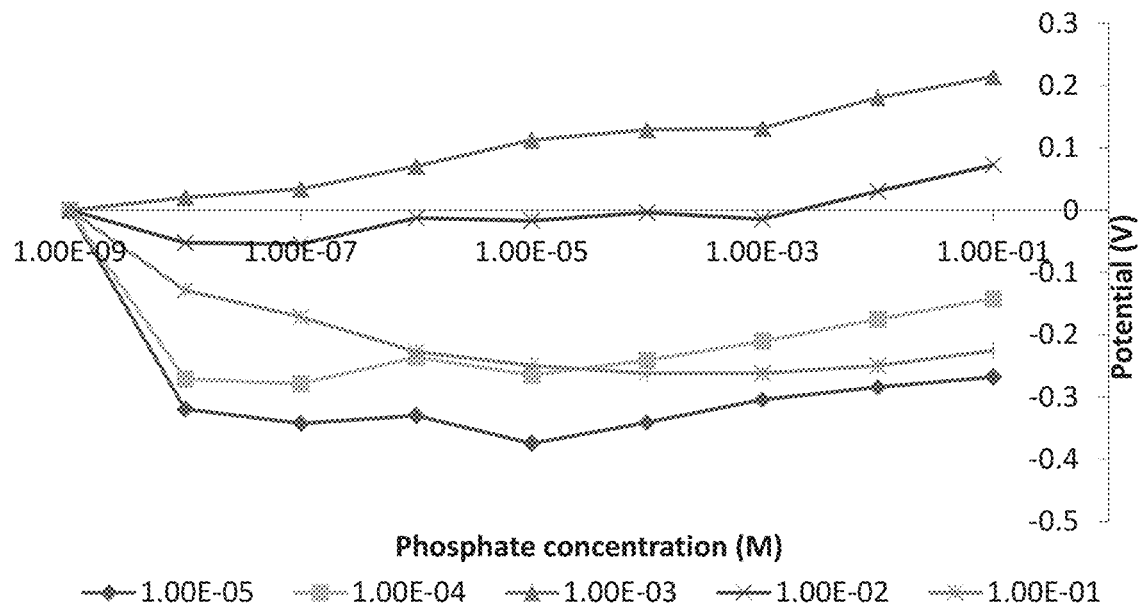
FIG. 15A and FIG. 15B are graphs illustrating phosphate detection using tin (IV) chloride in KH2PO4 aqueous solution at pH 4.5 (FIG. 15A) and an interference study (FIG. 15B) of phosphate ions in presence of Cl— ions [KCl with 10-3 to 10-1 (mol/L)] using tin (IV) chloride modified sensor.

Example 3. Tin (IV) Chloride Effects on Phosphate Sensing with an SPE Sensor Tin (IV) Chloride: As a new surface treatment material to detect phosphate, tin (IV) chloride was tested. Tin (IV) chloride dissolved in DI water was drop-casted on the working electrode and dried at room temperature. FIG. 15A shows the effect of tin (IV) chloride concentration on phosphate sensing. The sensor shows a linear response to the phosphate. The measured potentials were proportionally increased with the higher concentration of tin (IV) chloride, except 1E-2 and 1E-1. The optimum concentration of tin (IV) Chloride was determined to be 10-3 M (mol/L) with the lower detection limit of 10-8 M (mol/L).

Figure 15B:
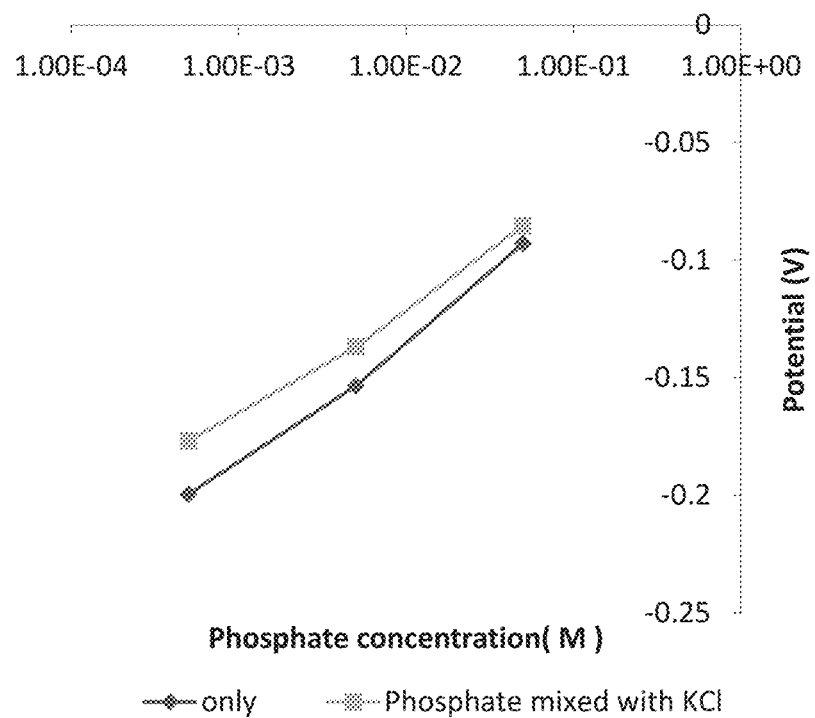

The interference with potassium chloride was also investigated (see FIG. 15B). KCl slightly increased the measured electrical potential of the tin (IV) chloride treated electrode. Tin (IV) chloride can be a good choice for phosphate detection as the sensor showed low potential interference in the presence of chlorine anion.

Figure 16:
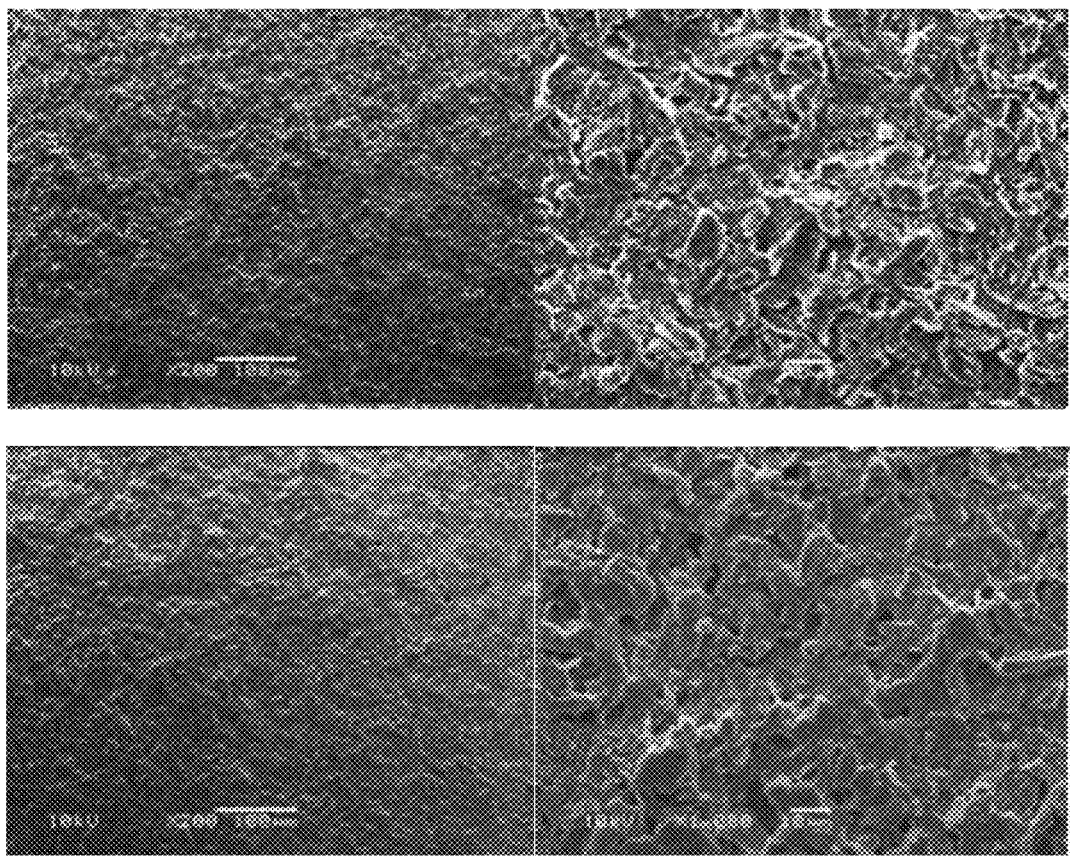
FIG. 16 is scanning electron microscopy (SEM) images of the tin (IV) chloride 10-3 M (mol/L) doped sensor surface (before use ×200, before use ×1000, after use ×1000, after use ×200 as clockwise rotation).

The SEM images show the surface of tin (IV) chloride (10-3 M mol/L) doped on the carbon electrode surface (see FIG. 16). No significant effect was observed on the sensor surface morphology other than the presence of phosphate in sensor after testing in phosphate solution.

Tin (IV) Chloride with Graphene Oxide and Pyrrole: Tin (IV) Chloride showed good interference characteristics but the potential range respect to the phosphate concentrations was not satisfactory. For better selectivity, Graphene oxide and pyrrole were combined with Tin (IV) Chloride as done on cobalt oxide nanoparticles. As described in the fabrication method, seven different sets of layers and mixtures using the GO, Py and SnCl4 were tested. Mixtures of the three components, mixtures of Py and Tin (IV) chloride, and 2 layers of reduced GO with mixture of Py and Tin (IV) chloride showed acceptable sensitivity and lower detection limits of 10-10 M. Only the three-layer combinations, namely Graphene Oxide-Polypyrrole-Tin (IV) Chloride (3 layers) and Reduced Graphene Oxide-Polypyrrole-Tin (IV) Chloride (3 layers), showed good linearity with the range of concentrations of phosphate ions (FIG. 14). The lower detection limit was determined 10-11 M (mol/L).

Thus, Tin (IV) chloride is an appropriate molecule to treat the surface of the sensor electrode for phosphate detection, especially due to the outstanding low detection limit.

Figure 17:
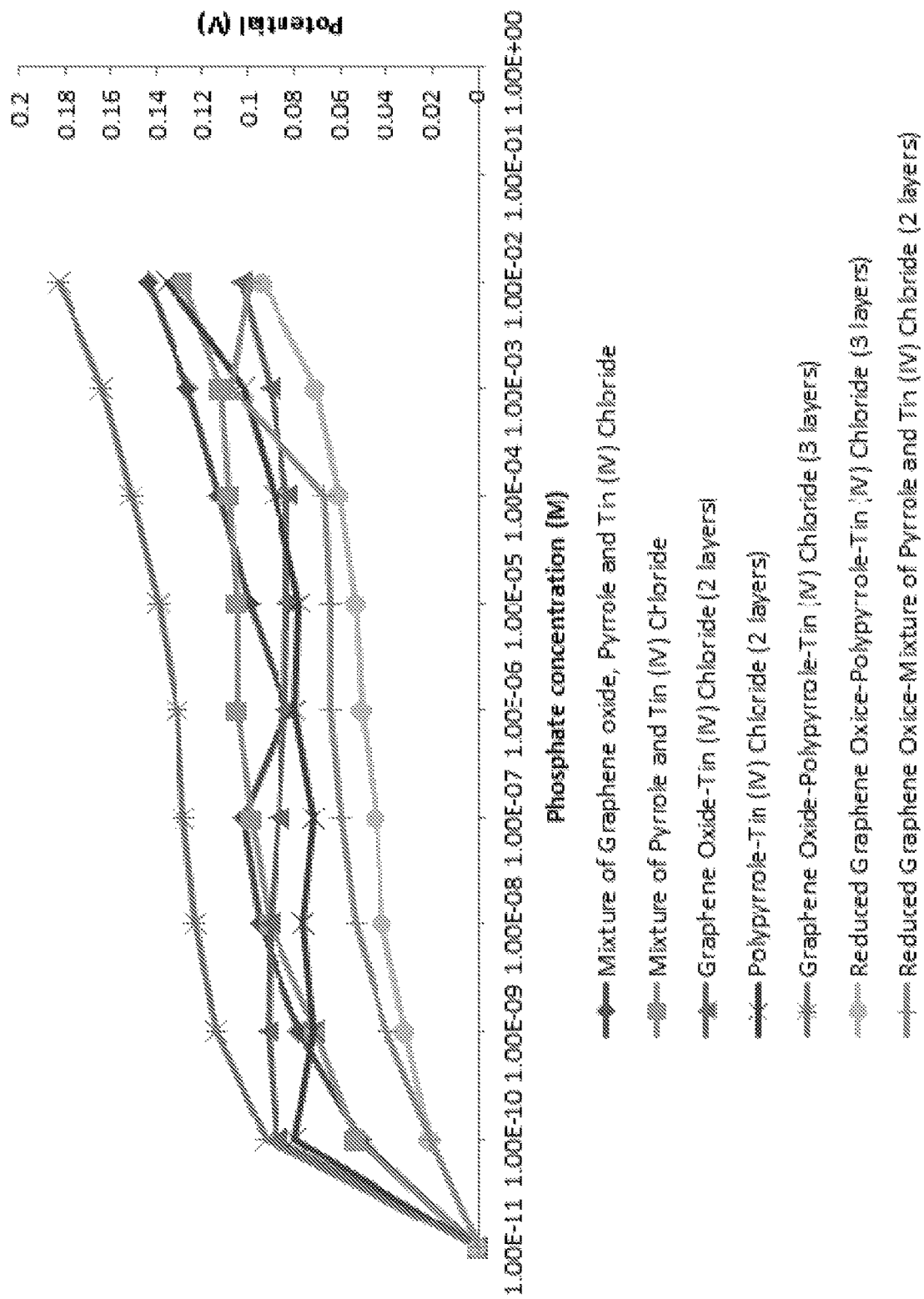
FIG. 17 is a graph illustrating phosphate detection using the tin (IV) chloride, graphene oxide, pyrrole combination in KH2PO4 aqueous solution at pH 4.5.
Figure 18A:
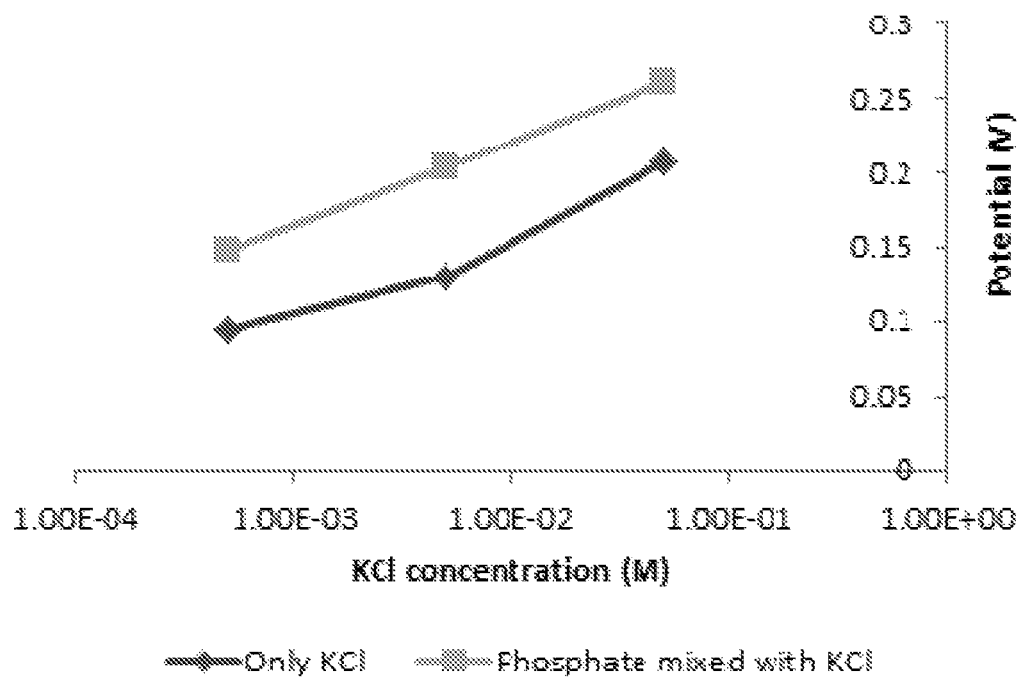
FIG. 18A and FIG. 18B are graphs illustrating an interference study of phosphate ions in presence of Cl— ions using graphene oxide-polypyrrole-tin (IV) chloride (FIG. 18A) and reduced graphene oxide-polypyrrole-tin (IV) chloride (FIG. 18B) modified screen printed electrode.
Figure 18B:
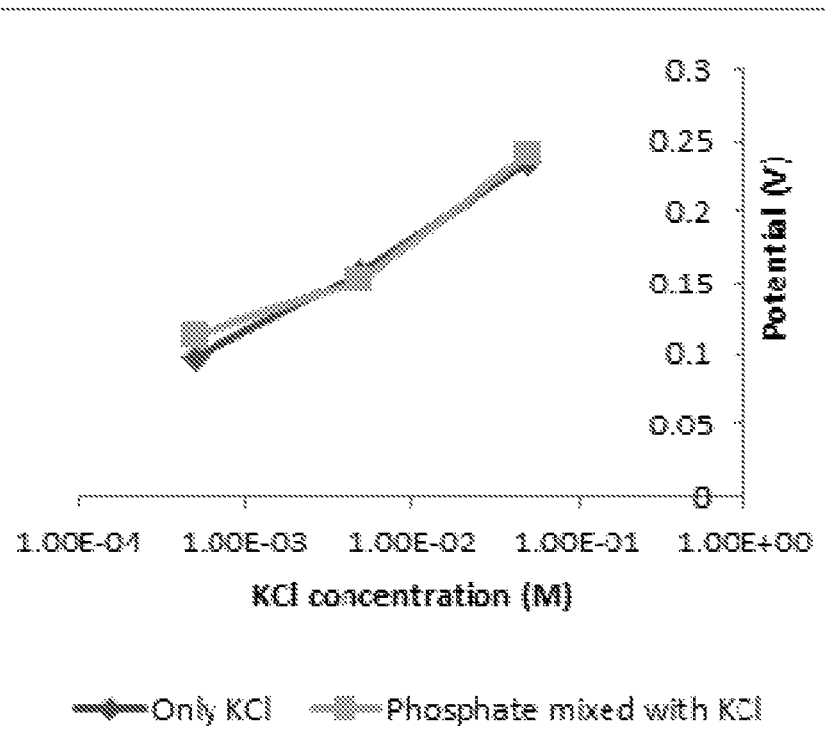
Figure 19A:
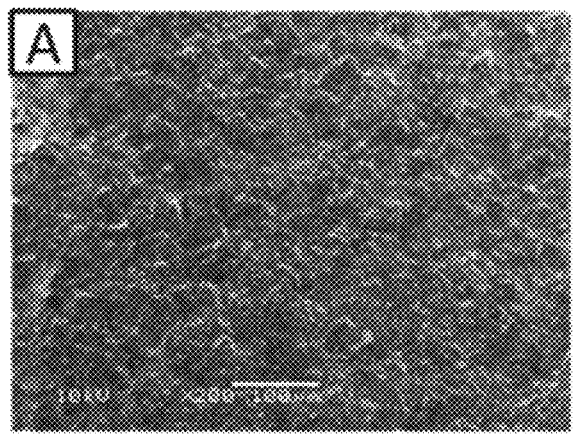
FIGS. 19A-19H are scanning electron microscopy (SEM) images of the Graphene Oxide-Polypyrrole-Tin (IV) Chloride (FIGS. 19A-19D) and Reduced Graphene Oxide-Polypyrrole-Tin (IV) Chloride (FIGS. 19E-19H) modified screen printed electrode (A) before experiment ×200 magnification (FIG. 19A and FIG. 19E), before experiment ×1000 magnification (FIG. 19B and FIG. 19F), after experiment ×200 magnification (FIG. 19C and FIG. 19G) and after experiment ×1000 magnification (FIG. 19D and FIG. 19H).
Figure 19B:
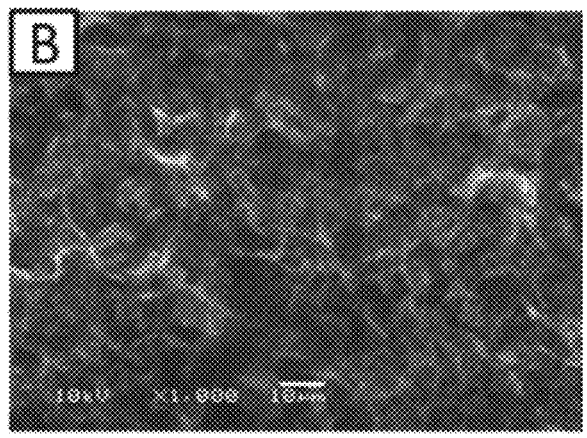
Figure 19C:
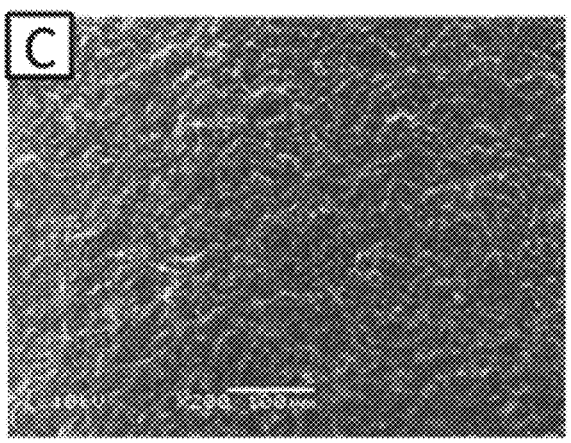
Figure 19D:
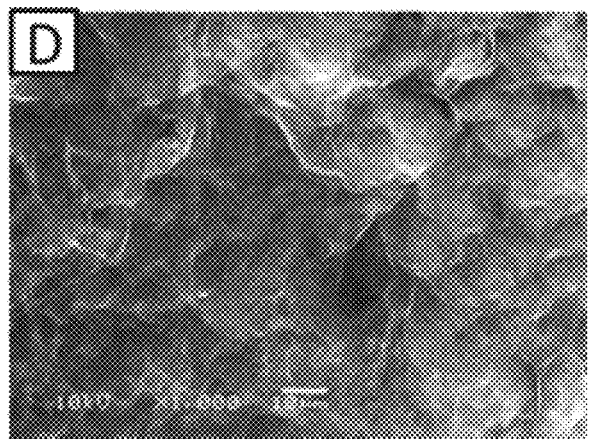
Figure 19E:
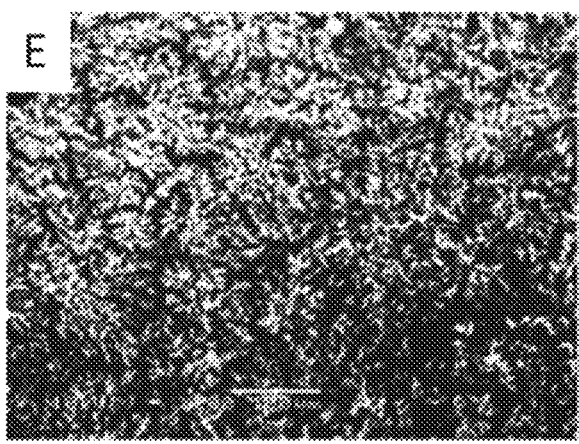
Figure 19F:
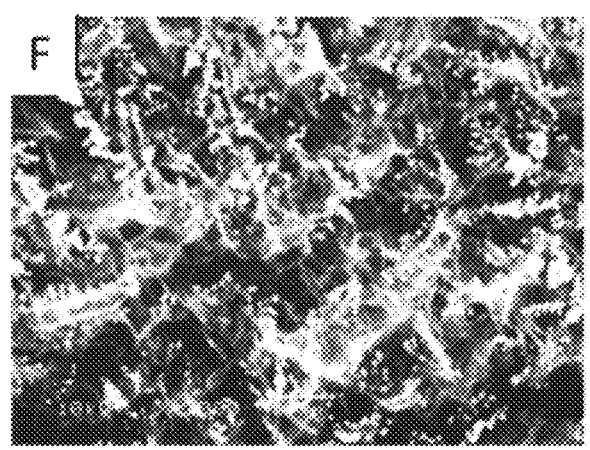
Figure 19G:
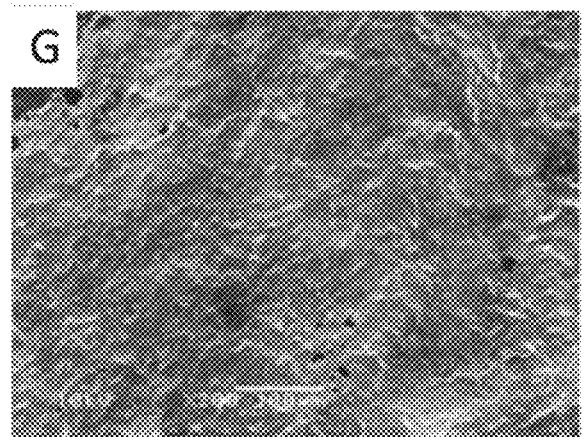
Figure 19H:
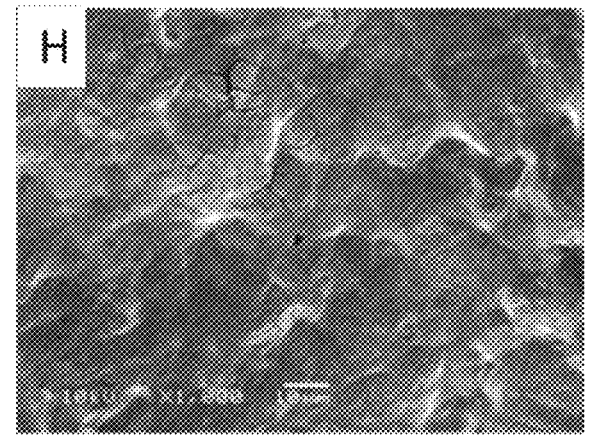

However, the interference from KCl was still observed. Thus, this interference limits the application of the Tin (IV) chloride in phosphate detection. The signal interference in the presence of chloride anions with phosphate sensor using non-reduced graphene oxide layered with pyrrole and tin (IV) chloride showed significant potential difference (see FIG. 18A). Though this sensor showed very good linear behavior, this method might not be a very useful option because of the potential interference. With the similar structure but with reduced graphene oxide, the lower detection limit was determined 10-11 M (mol/L) (see FIG. 17) with a very good interference characteristic in presence of chloride ions (see FIG. 18B).

FIGS. 19A-19H show the scanning electron microscopy (SEM) images of the graphene oxide-polypyrrole-tin (IV) chloride (FIGS. 19A-19D) and reduced graphene oxide-polypyrrole-tin (IV) chloride (FIGS. 19E-19H) modified screen printed electrode before and after use of the detection of phosphate in water. Reduction of GO caused the removal of the functionalized oxygen group and created wrinkles on the surface of the SPE sensor.

Example 4. Diphenyltin Dichloride Effects on Phosphate Sensing with an SPE Sensor Diphenyltin Dichloride: Since tin (IV) chloride shows good sensitivity, diphenyltin dichloride was also examined in phosphate detection. There was no steady pattern from the OCPT signal. However, the investigation of diphenyltin dichloride with several substituents in the para position of the benzene ring indicated an increase in the phosphate selectivity.

Figure 20:
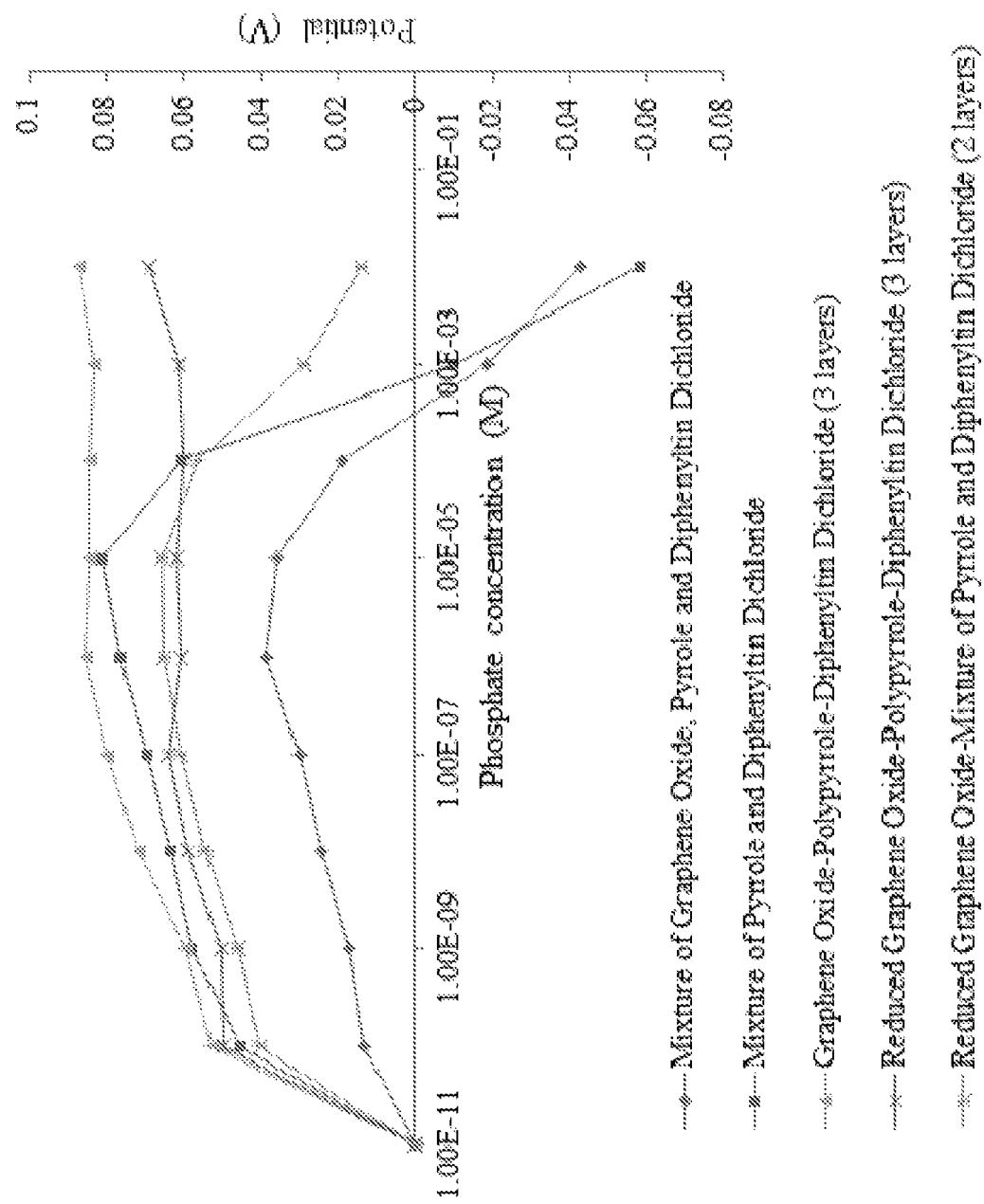
FIG. 20 is a graph illustrating phosphate detection using the diphenyltin dichloride, graphene oxide, pyrrole combination in KH2PO4 aqueous solution at pH 4.5.
Figure 21A:
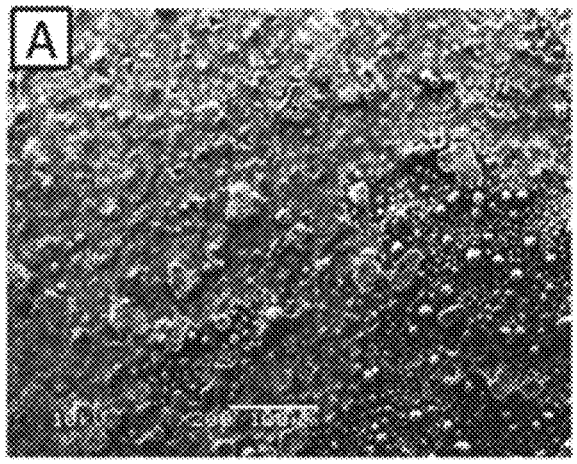
FIGS. 21A-21D are scanning electron microscopy (SEM) images of the Graphene Oxide-Polypyrrole-Diphenyltin Dichloride modified SPE before experiment ×200 magnification (FIG. 21A), before experiment ×1000 magnification (FIG. 21B), after experiment ×200 magnification (FIG. 21C), after experiment ×1000 magnification (FIG. 21D).
Figure 21B:
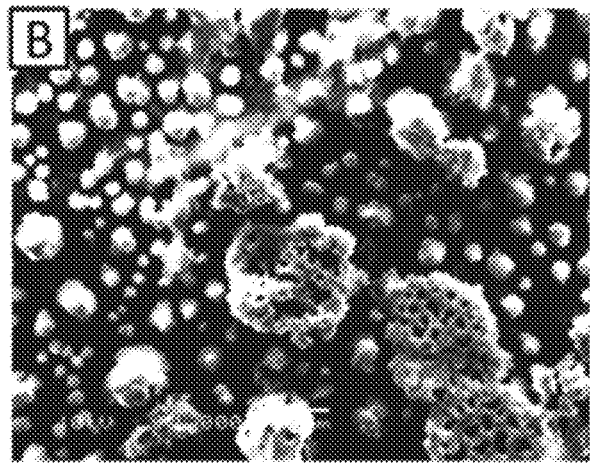
Figure 21C:
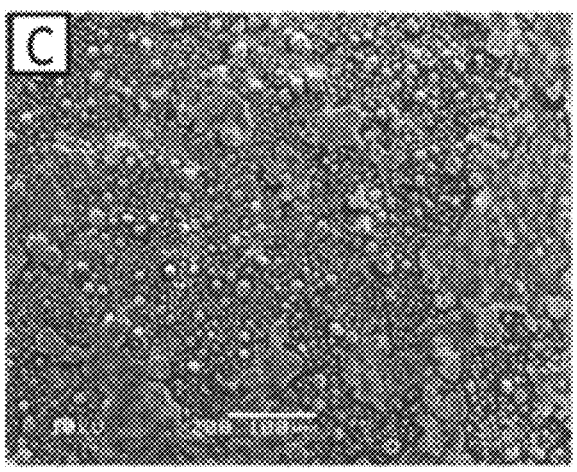
Figure 21D:
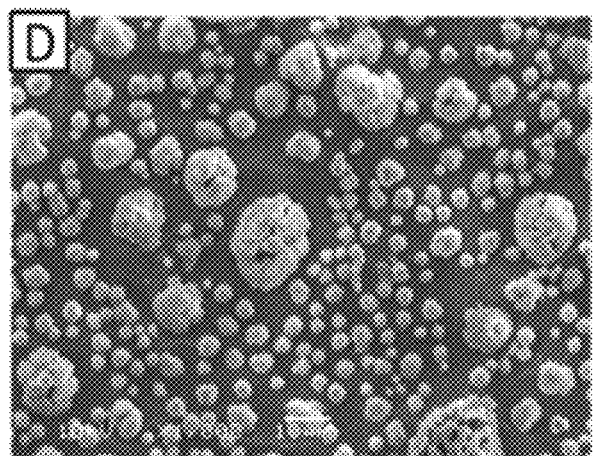
Figure 22:
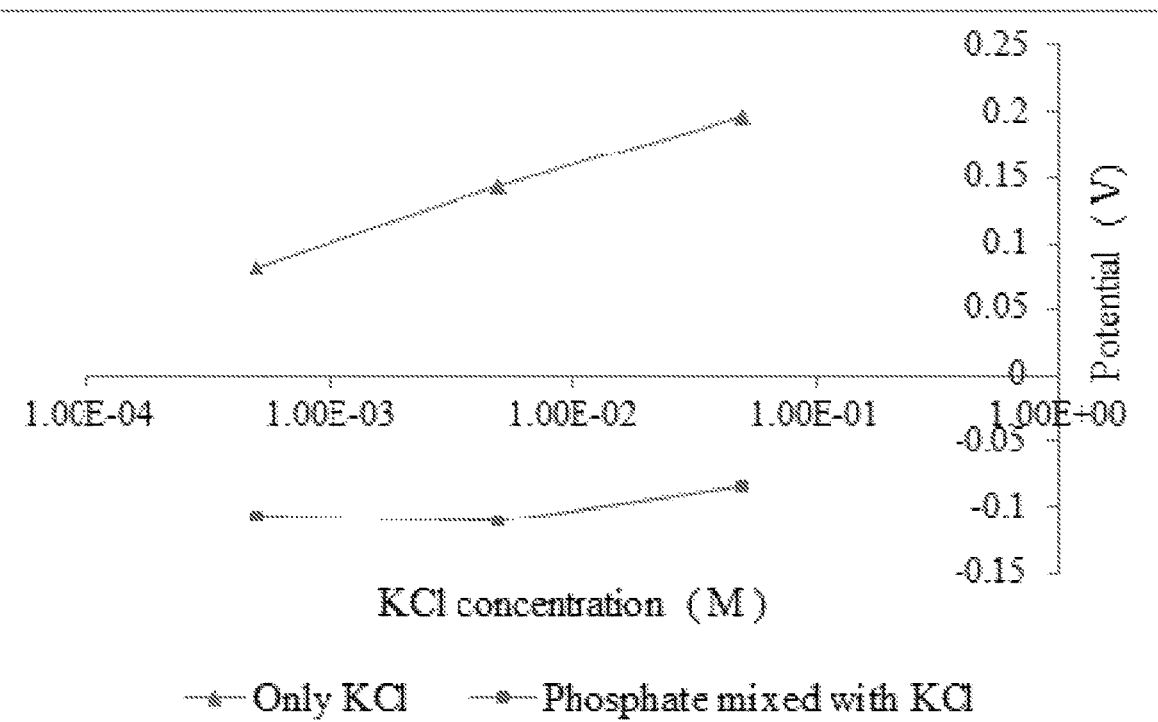
FIG. 22 is a graph illustrating an interference study of phosphate ions in presence of Cl— ions using graphene oxide-polypyrrole-diphenyltin dichloride.

Diphenyltin Dichloride with Graphene Oxide and Pyrrole: For better selectivity, graphene oxide and pyrrole were combined with diphenyltin dichloride. The mixture of all three components showed relatively lower sensitivity in comparison to the others. However, all combinations showed similar low detection limits of 10-10 M, which was similar to the sensors with tin (IV) chloride. From the five different combination sets, only the graphene oxide-polypyrrole-diphenyltin dichloride (3 layers) showed a steady growth toward the higher concentration of phosphate ions (see FIG. 20). But, the signals were mostly remaining flat for phosphate concentrations between 10-6 M (mol/L) and 10-3 M (mol/L), indicating the sensors are not responsive to the phosphate concentrations higher than 10-6 M (mol/L). The interference study of this sensor showed a significant potential difference in the presence of chloride anions (see FIG. 22).

The scanning electron microscopy (SEM) images of the graphene oxide-polypyrrole-diphenyltin dichloride sensor are shown in FIGS. 21A-21D. The surface morphology of this sensor was completely different from the previous sensors.

Diphenyltin dichloride modified sensor may not be suitable for use in phosphate detection because of higher signal interference and unsteady potential respect to the concentration of the phosphate anions.

Figure 23A:
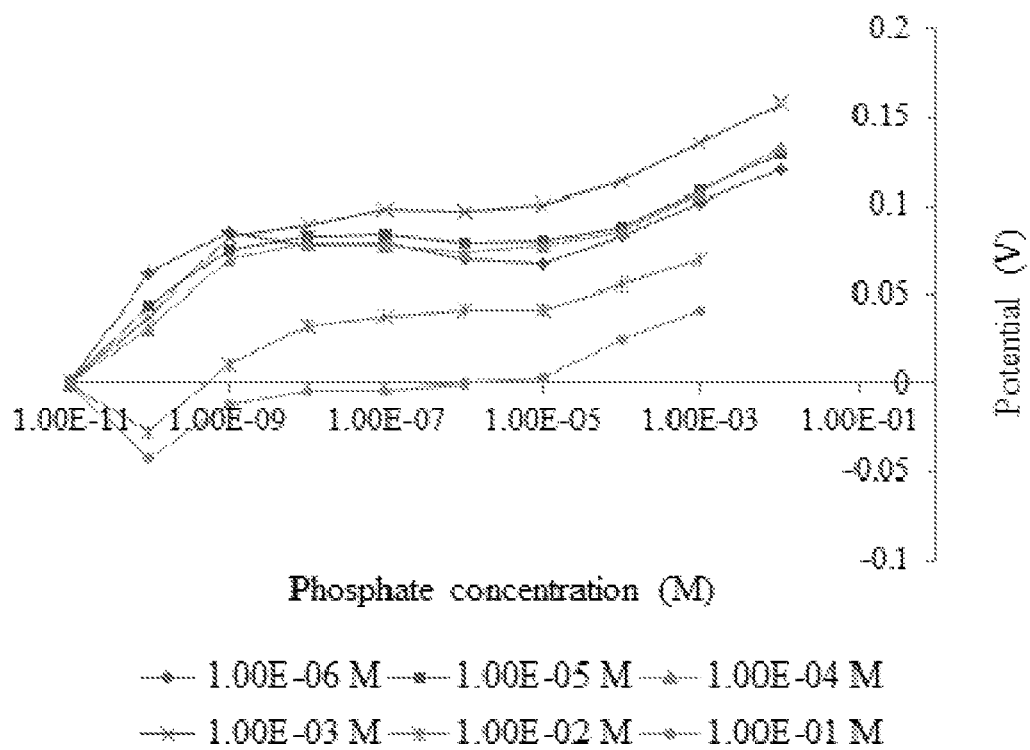
FIGS. 23A and 23B are graphs illustrating phosphate detection using ammonium molybdate modified SPE in KH2PO4 aqueous solution at pH 4.5 (FIG. 23A) and an interference study of phosphate ions in presence of Cl— ions using ammonium molybdate modified SPE (FIG. 23B).
Figure 23B:
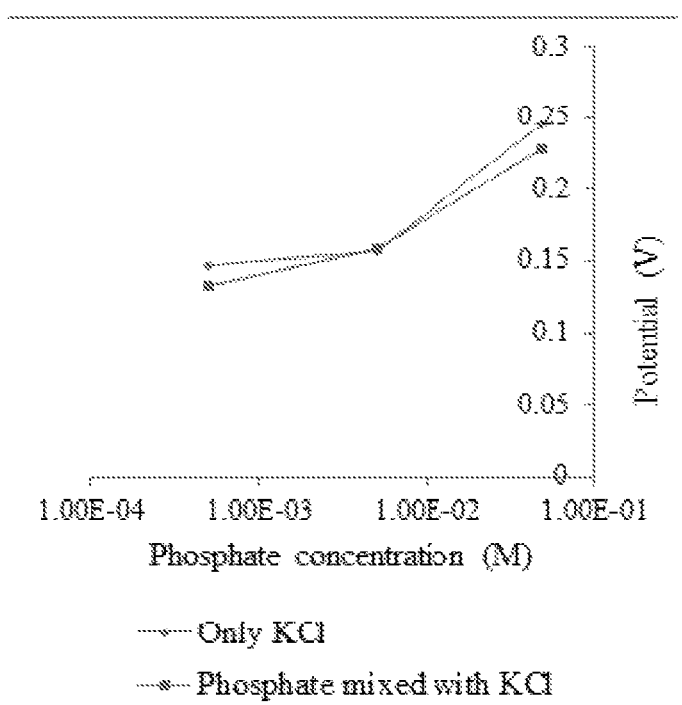
Figure 24A:
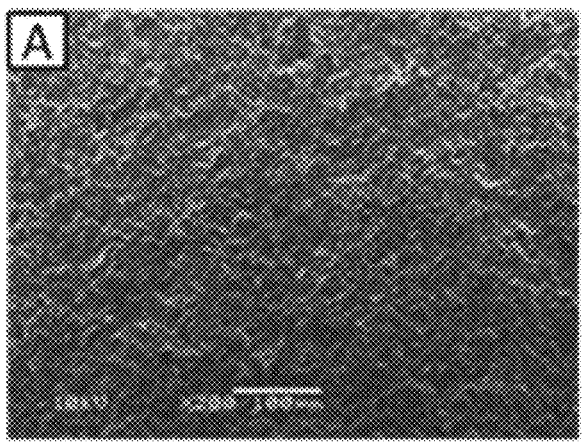
FIGS. 24A-24D are scanning electron microscopy (SEM) images of the ammonium molybdate modified SPE before experiment ×200 magnification (FIG. 24A), before experiment ×1000 magnification (FIG. 24B), after experiment ×200 magnification (FIG. 24C), after experiment ×1000 magnification (FIG. 24D).
Figure 24B:
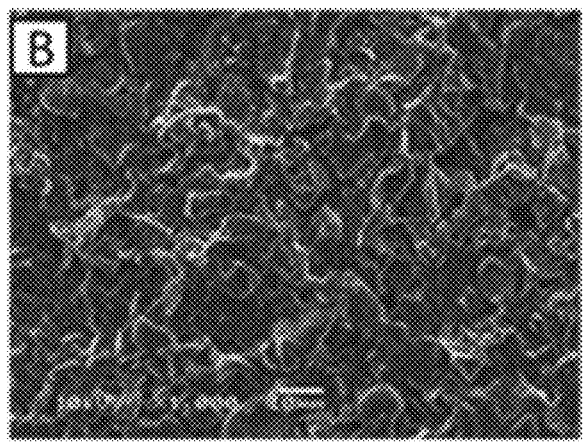
Figure 24C:
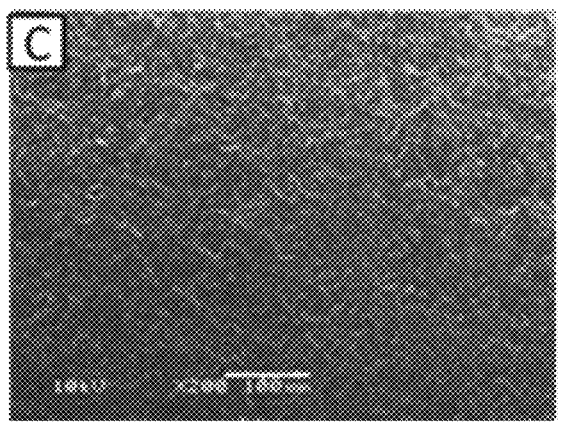
Figure 24D:
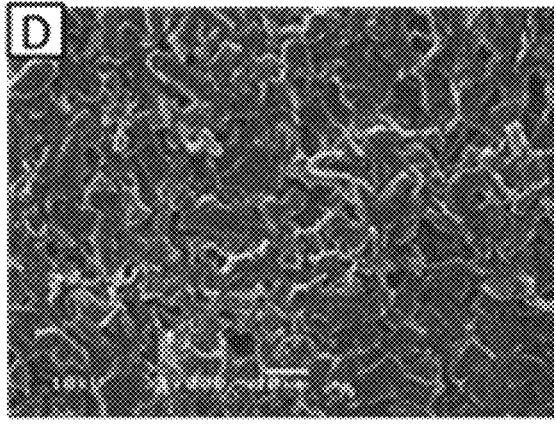

Example 5. Ammonium Molybdate Effects on Phosphate Sensing with an SPE Sensor Ammonium Molybdate: As another candidate molecule to detect phosphate, Ammonium molybdate was selected. Ammonium molybdate dissolved in DI water was drop-casted on the working electrode and then dried at room temperature. FIG. 23A shows the effect of concentration of ammonium molybdate on phosphate sensing using SPE sensor modified with only ammonium molybdate. The potentials proportionally increased with higher concentration of phosphate. From six different concentrations of ammonium molybdate, the optimum concentration was determined to be 10-3 (mol/L) with the lower detection limit of 10-11 M (mol/L), which was similar to the results seen with the sensors made of tin (IV) chloride or diphenyltin dichloride.

The potential interference from potassium chloride on the ammonium molybdate phosphate sensor was also investigated. The signal interference between the potassium chloride solution and the phosphate solution was very low over the tested KCl concentrations (see 23B), especially in comparison to the other sensors tested in Examples 2-4 described above.

The ammonium molybdate sensor surface was studied using SEM. The SEM images showed no significant effect on the sensor surface before and after experiment (see FIGS. 24A-24D).

Figure 25:
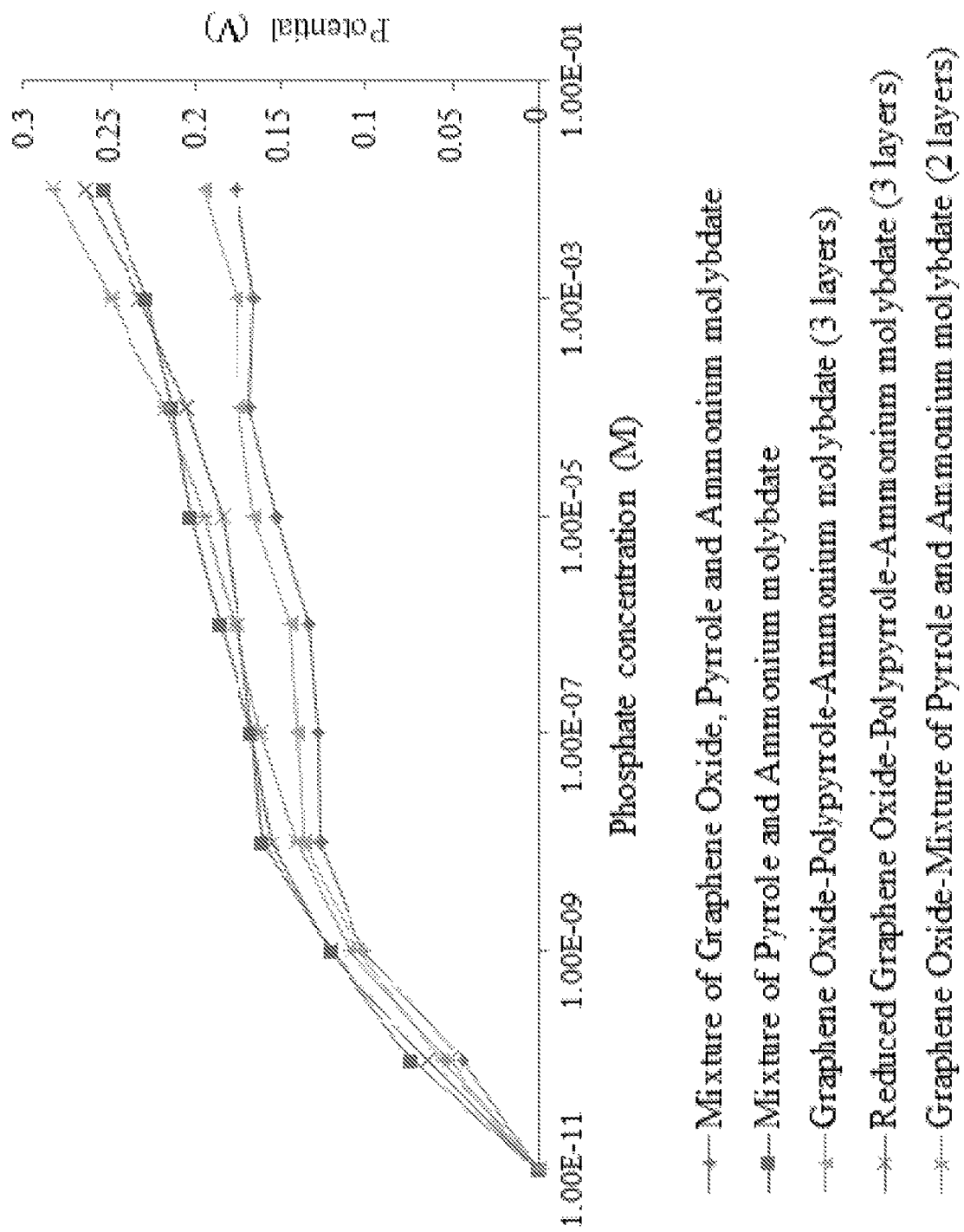
FIG. 25 is a graph illustrating phosphate detection using graphene oxide, pyrrole and ammonium molybdate modified SPE in KH2PO4 aqueous solution at pH 4.5.

Ammonium Molybdate with Graphene Oxide and Pyrrole: Graphene oxide and pyrrole were combined with ammonium molybdate solution to improve the sensitivity and detection limit for phosphate sensing. Five different sets of combinations with ammonium molybdate, Graphene Oxide and Pyrrole were tested in phosphate detection in aqueous solution at pH 4.5. In general, all the sensors had better sensitivity and linearity in comparison to the other sensors tested. Among the five different ammonium molybdate nanocomposite modified sensors, the mixture of pyrrole and ammonium molybdate, reduced graphene oxide-polypyrrole-ammonium molybdate (3 layers), Graphene Oxide-Mixture of Pyrrole and Ammonium molybdate (2 layers) displayed the best linear behavior (see FIG. 25).

Figure 26A:
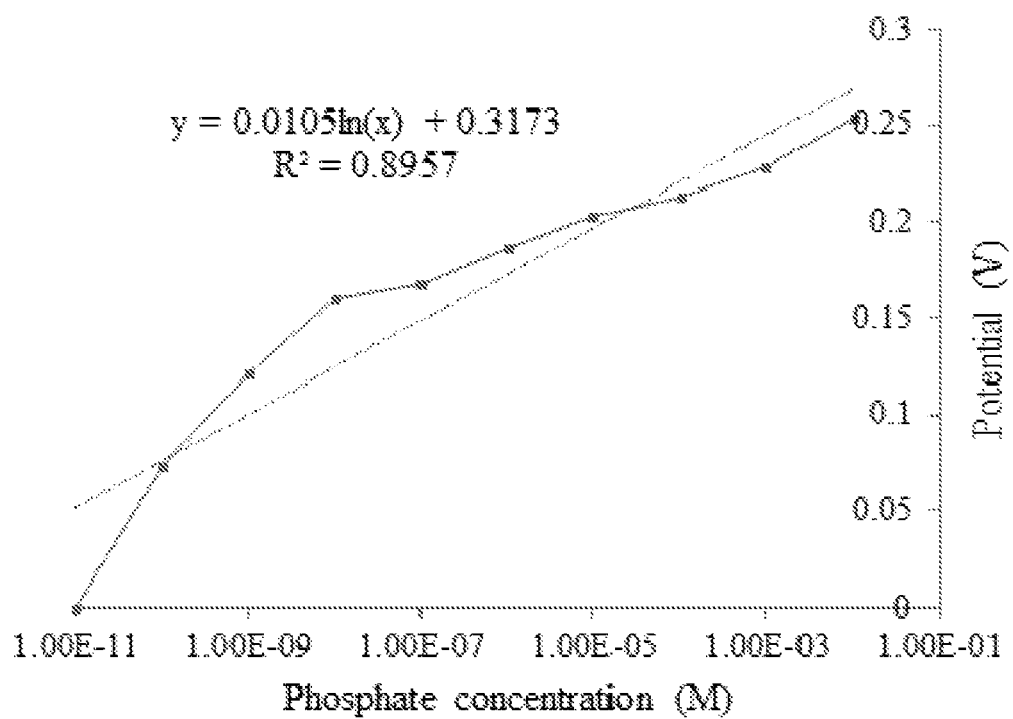
FIGS. 26A and 26B are graphs illustrating phosphate detection using mixture of pyrrole and ammonium molybdate modified SPE in KH2PO4 aqueous solution at pH 4.5
Figure 26B:
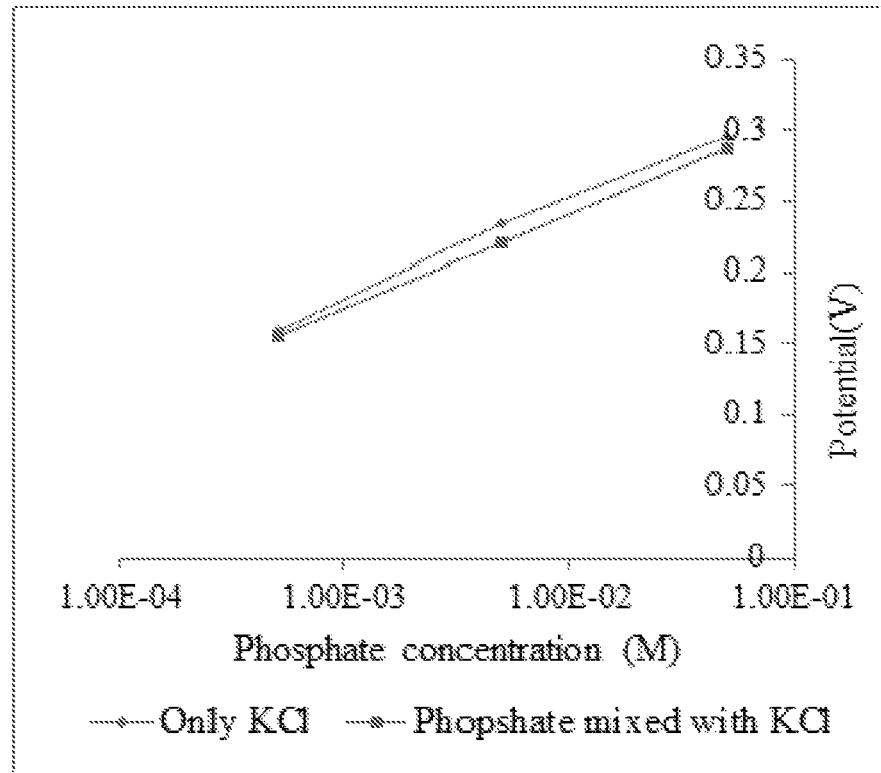

The optimized mixture of pyrrole (0.2 M) and ammonium molybdate (2×10-3 mol/L) showed good linearity with the phosphate concentrations (see FIG. 26A). The low detection limit was determined to be 10-11 mol/L with $R^2=0.8957$. The potential interference using this sensor in the presence of chloride ions showed a small deviation comparing with the signal from phosphate solution without any other anions (see FIG. 26B).

Figure 27A:
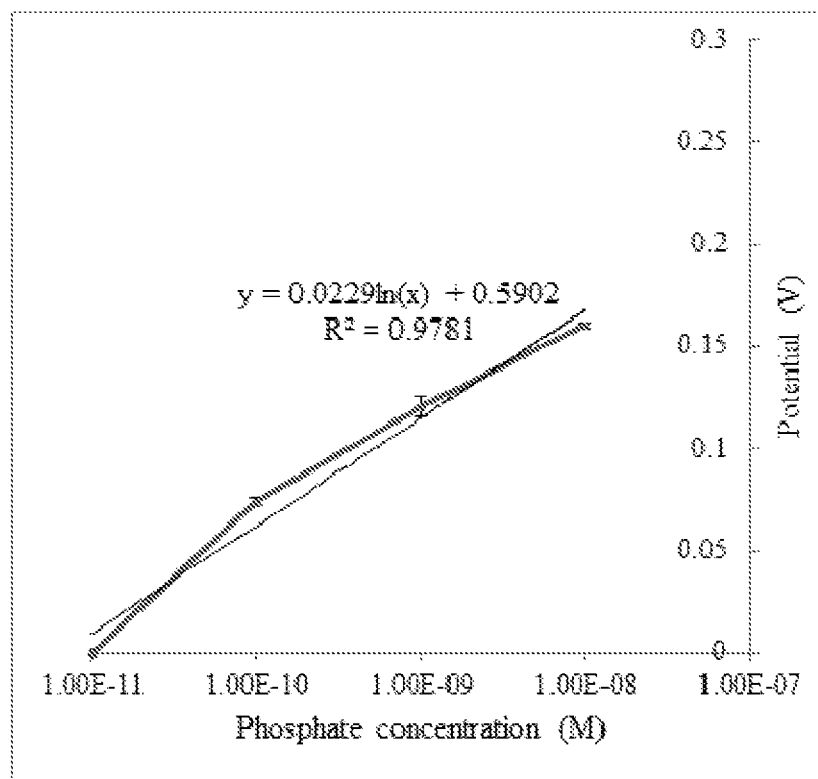
FIGS. 27A and 27B are graphs illustrating phosphate detection using mixture of pyrrole and ammonium molybdate modified SPE in KH2PO4 aqueous solution at pH 4.5 in 10-11 to 10-8 (mol/L) (FIG. 27A) and 10-8 to 10-2 (mol/L) (FIG. 27B).
Figure 27B:
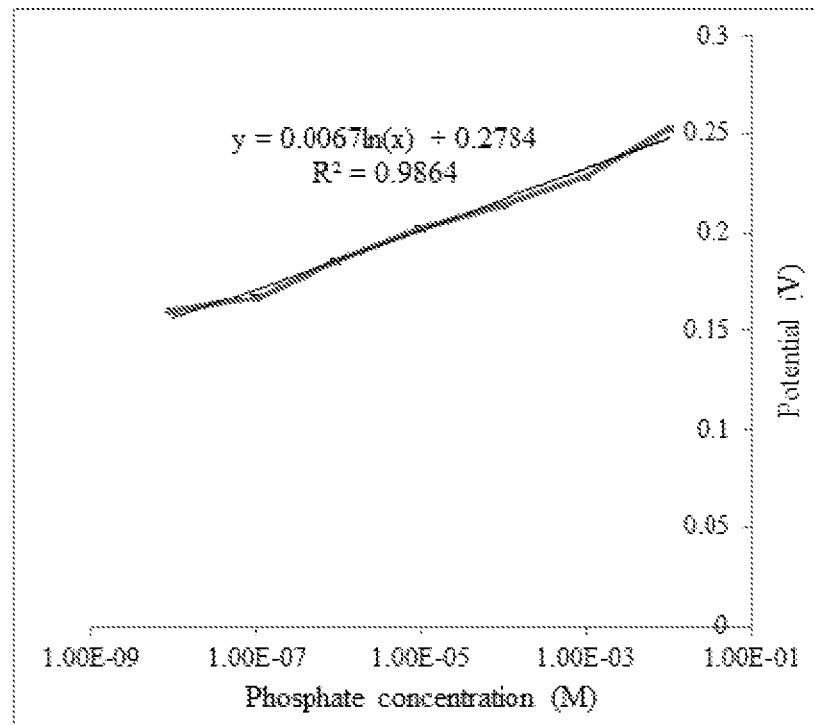

Graphene Oxide, Pyrrole and Ammonium molybdate was used to modify the surface of the working electrode as layers (Graphene Oxide: 1 mg/mL, Polypyrrole: 0.1 M and Ammonium molybdate: 2×10-3 mol/L) as well as the reduced Graphene Oxide with the same concentration of all three components. In both cases signal rose linearly at the beginning and the end, with the fluctuations observed near the mid-range of the concentrations of the phosphate solutions (see FIGS. 27A and 27B). The interference test showed little signal difference when tested in presence of chloride anions. The OCPT response in two ranges of phosphate concentration showed improved calibration curve (logarithmic fit) with $R^2=0.9781$ and $R^2=0.9864$ for 10-11 to 10-8 mol/L and 10-8 to 10-2 mol/L, respectively.

Figure 28A:
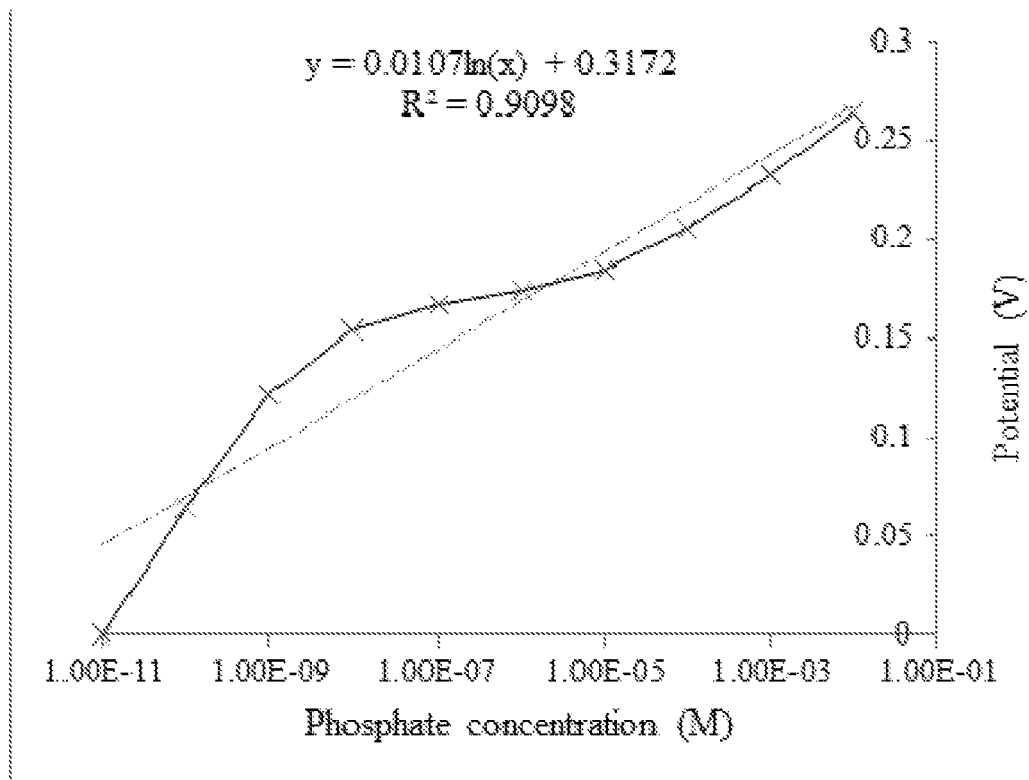
FIG. 28A and FIG. 28B are graphs illustrating phosphate detection using reduced graphene oxide-mixture of pyrrole and ammonium molybdate (2 layers) modified SPE in KH2PO4 aqueous solution at pH 4.5 (FIG. 28A), and an interference study of phosphate ions in presence of Cl— ions (FIG. 28B).
Figure 28B:
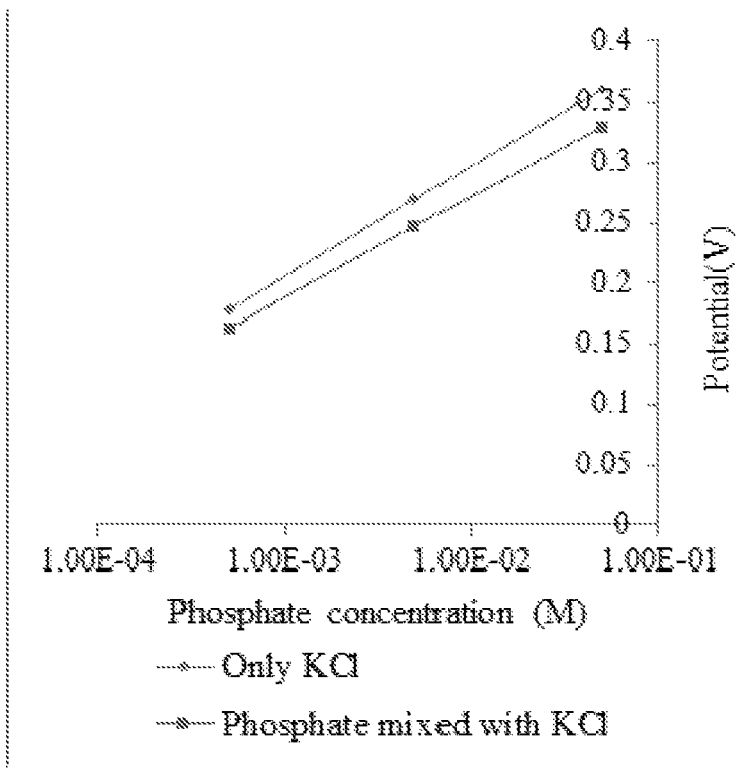

The limit of detection was determined to be 10-11 M (mol/L) with $R^2=0.9098$ for the sensor modified with the reduced Graphene Oxide-mixture of Polypyrrole and Ammonium molybdate (2 layers) (see FIG. 28A). The interference test of this sensor also showed a very slight deviation when tested in presence of potassium chloride (see FIG. 28B).

Figure 29A:
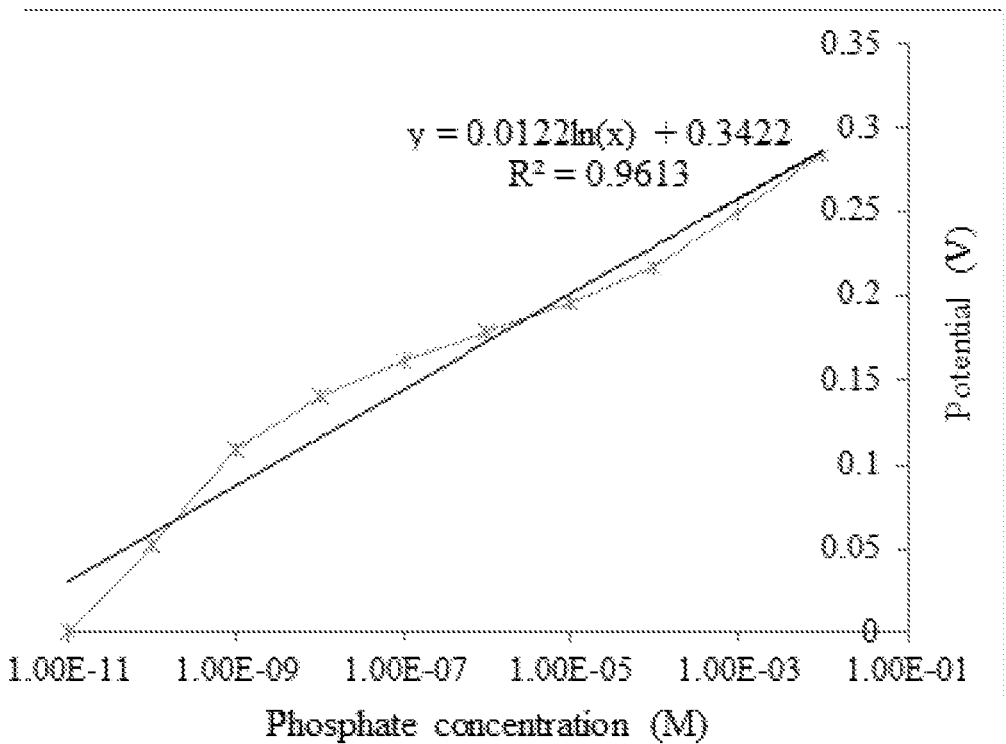
FIG. 29A and FIG. 29B are graphs illustrating phosphate detection using graphene oxide-mixture of pyrrole and ammonium molybdate (2 layers) modified SPE in KH2PO4 aqueous solution at pH 4.5 (FIG. 29A), and an interference test in the presence of Cl— (FIG. 29B).

Phosphate detection using Graphene Oxide-mixture of Pyrrole and Ammonium molybdate (2 layers) showed the best logarithmic fit with $R^2=0.9613$. The limit of detection was determined 10-11 M (mol/L) (see FIG. 29A) and the with the calibration curve limit of detection will be 10-12 M (mol/L).

Figure 29B:
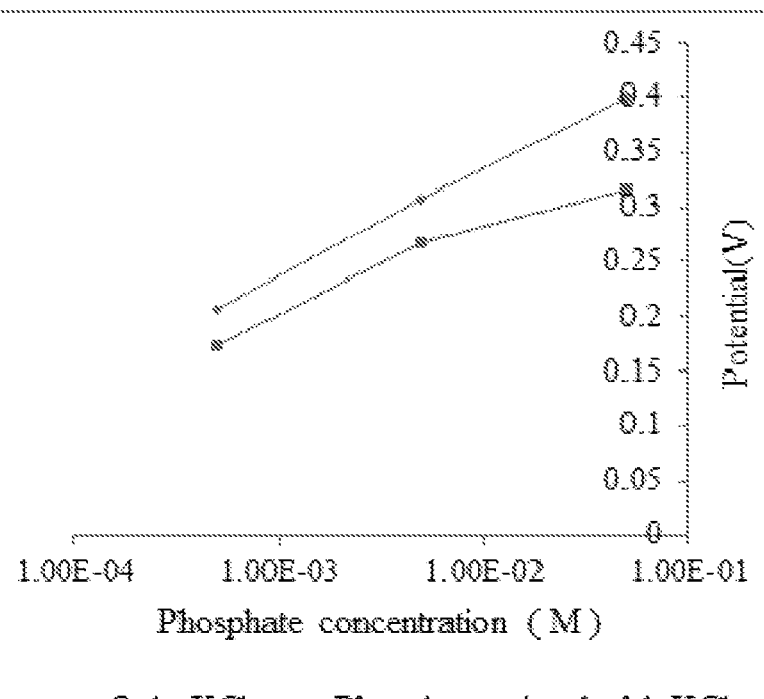
Figure 30A:
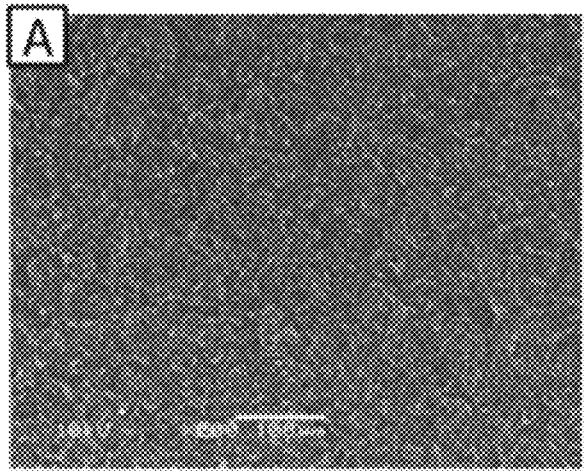
FIGS. 30A-30L are scanning electron microscopy (SEM) images of the mixture of pyrrole and ammonium molybdate (FIGS. 30A-30D), reduced graphene oxide-polypyrrole-ammonium molybdate (3 layers) (FIGS. 30E-30H), graphene oxide-mixture of Pyrrole and ammonium molybdate (2 layers) (FIGS. 30I-30L) modified SPEs before experiment ×200 magnification (FIG. 30A, FIG. 30E, and FIG. 30I), before experiment ×1000 magnification (FIG. 30B, FIG. 30F, and FIG. 30J), after experiment ×200 magnification (FIG. 30C, FIG. 30G, and FIG. 30K), after experiment ×1000 magnification (FIG. 30D, FIG. 30H, and FIG. 30L).
Figure 30B:
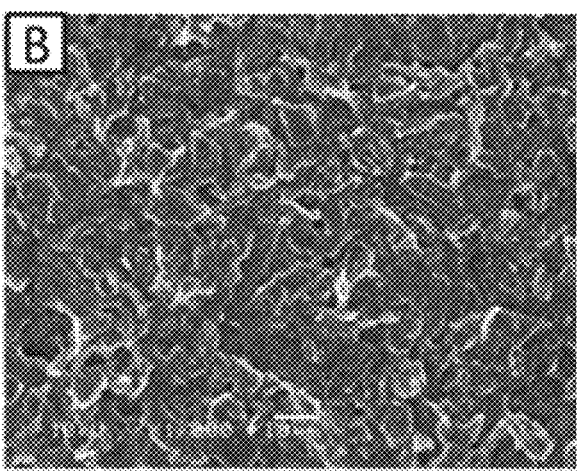
Figure 30C:
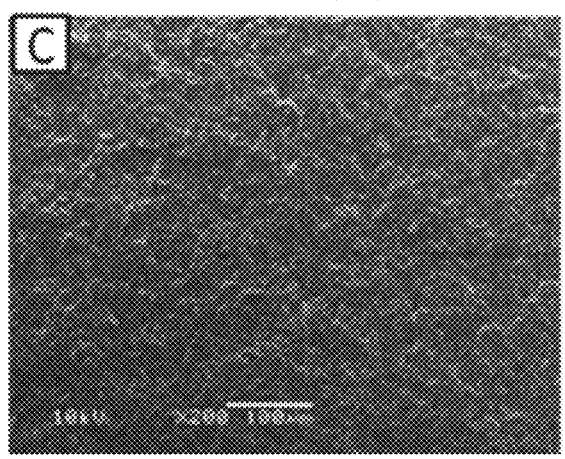
Figure 30D:
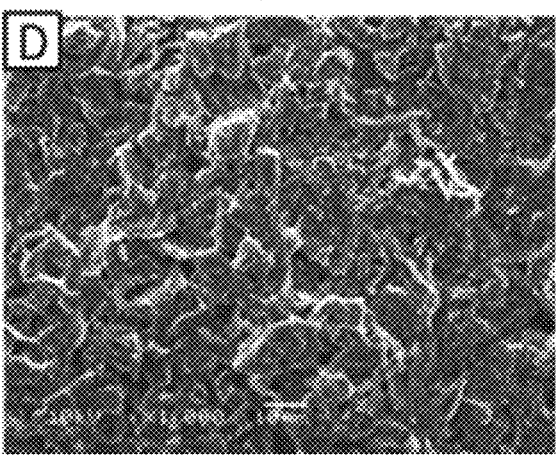
Figure 30E:
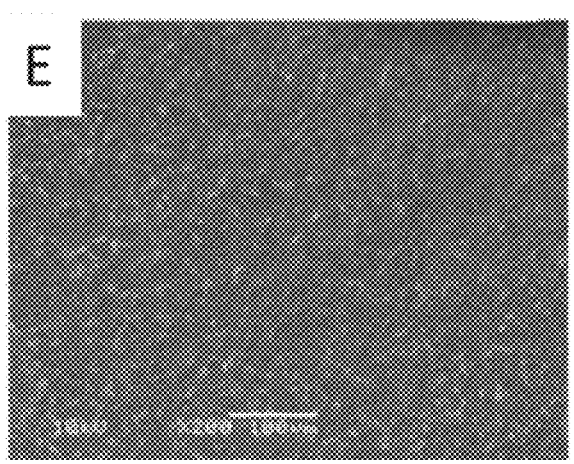
Figure 30F:
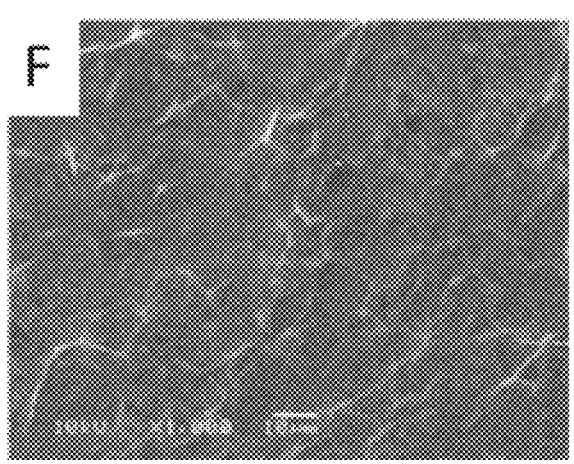
Figure 30G:
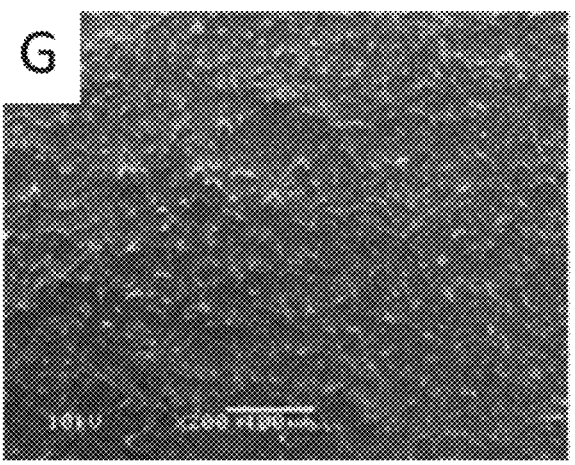
Figure 30H:
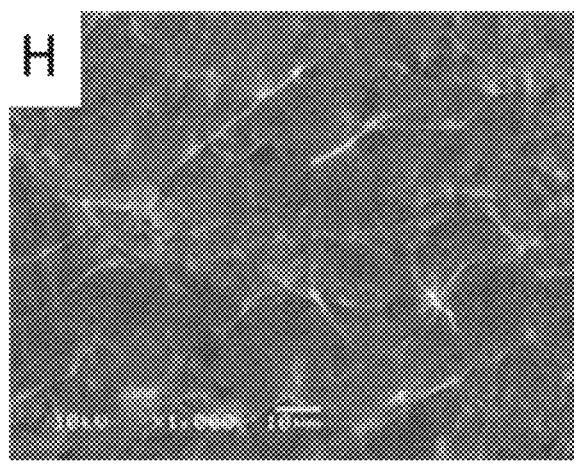
Figure 30I:
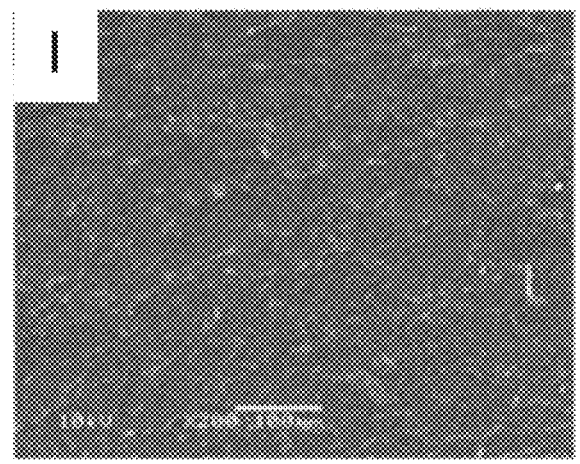
Figure 30J:
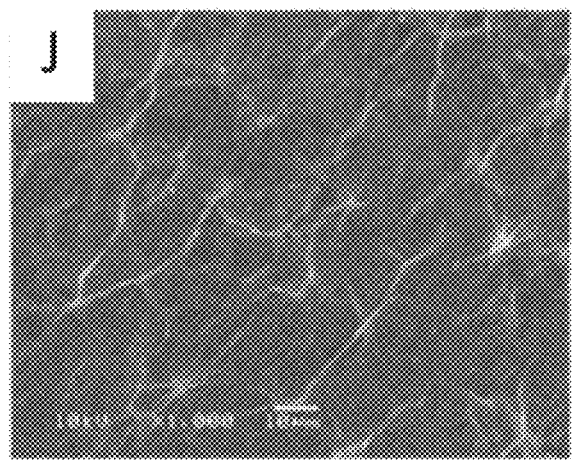
Figure 30K:
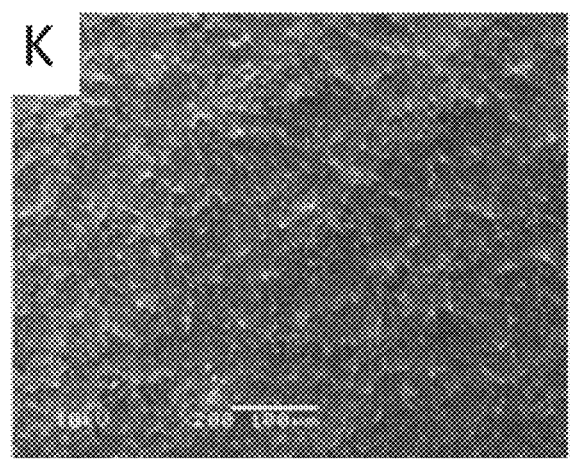
Figure 30L:
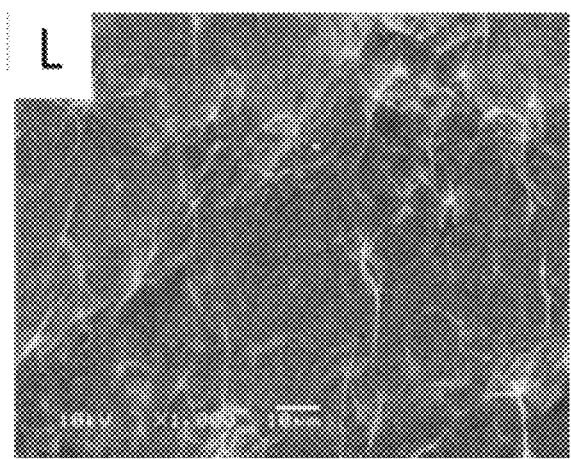

A slight deviation was observed from the interference test of this sensor also showed a slight deviation when tested in phosphate and phosphate presence with potassium chloride with chloride anion (see FIG. 29B).

The SEM images of the SPE modified with Ammonium molybdate, Graphene Oxide and Pyrrole sensor surface shows the difference between the combinations of the compounds used was studied using scanning electron microscopy (SEM) images (see FIGS. 30A-30L). The SEM images (FIGS. 30A-30L) show that the sensor with reduced Graphene Oxide-Polypyrrole-Ammonium molybdate (3 layers) (FIGS. 30E-30H) and Graphene Oxide-Mixture of Pyrrole and Ammonium molybdate (2 layers) (FIGS. 30I-30L) have larger surface areas. Graphene Oxide and reduced Graphene Oxide sheets served as a template for deposition of the Pyrrole and Ammonium molybdate that improved sensitivity (see FIG. 25).

Various embodiments and features are set forth in the following claims.

What is claimed is:

1. An electrode for phosphate sensing comprising
   a conductive layer;
   a first layer electrically connected to the conductive layer, wherein the first layer includes a first component selected from a group consisting of tin (IV) chloride, diphenyl tin dichloride, and ammonium molybdate;
   a second layer electrically connected to the conductive layer, wherein the second layer is located between the conductive layer and the first layer, wherein the second layer includes a second component, and wherein the second component is graphene oxide or reduced graphene oxide; and
   a third layer electrically connected to the first layer and the second layer, wherein the third layer is located between the first layer and the second layer, wherein the third layer includes a third component, and wherein the third component is pyrrole or polypyrrole.

2. The electrode of claim 1, wherein the first component is ammonium molybdate, wherein the second component is reduced graphene oxide, and wherein the third component is polypyrrole.

3. A sensor for detecting phosphate comprising:
   a counter electrode;
   a reference electrode; and
   a working electrode including the electrode of claim 1.

4. The sensor of claim 3, wherein the working electrode is a screen-printed electrode.

5. An electrode for phosphate sensing comprising:
   a conductive layer;
   a first layer electrically connected to the conductive layer, wherein the first layer includes a first component homogeneously mixed with pyrrole, the first component being selected from a group consisting of cobalt oxide nanoparticles, tin (IV) chloride, diphenyl tin dichloride, and ammonium molybdate; and
   a second layer electrically connected to the conductive layer, wherein the second layer is located between the conductive layer and the first layer, wherein the second layer includes a second component, and wherein the second component is graphene oxide or reduced graphene oxide.

6. The electrode of claim 5, wherein the first component is ammonium molybdate, and wherein the second component is reduced graphene oxide.

7. A sensor for detecting phosphate comprising:
   a counter electrode;
   a reference electrode; and
   a working electrode including the electrode of claim 5.

8. The sensor of claim 7, wherein the working electrode is a screen-printed electrode.

* * * * *